(12) United States Patent
Schembre et al.

(10) Patent No.: US 11,986,199 B2
(45) Date of Patent: May 21, 2024

(54) GRASPING DEVICE FOR INDEPENDENT TISSUE MANIPULATION DURING GASTROINTESTINAL ENDOSCOPIC PROCEDURES AND METHODS OF USE

(71) Applicant: EndoGear LLC, Olympia, WA (US)

(72) Inventors: Drew Schembre, Olympia, WA (US); Benjamin Merrifield, Olympia, WA (US)

(73) Assignee: EndoGear, LLC, Olympia, WA (US)

(*) Notice: Subject to any disclaimer, the term of this patent is extended or adjusted under 35 U.S.C. 154(b) by 431 days.

(21) Appl. No.: 17/063,614

(22) Filed: Oct. 5, 2020

(65) Prior Publication Data

US 2022/0015787 A1 Jan. 20, 2022

Related U.S. Application Data

(60) Provisional application No. 63/052,464, filed on Jul. 16, 2020.

(51) Int. Cl.
| | |
|---|---|
| *A61B 17/29* | (2006.01) |
| *A61B 1/00* | (2006.01) |
| *A61B 1/018* | (2006.01) |
| *A61B 10/06* | (2006.01) |
| *A61B 17/00* | (2006.01) |

(52) U.S. Cl.
CPC .......... *A61B 17/29* (2013.01); *A61B 1/00066* (2013.01); *A61B 1/00082* (2013.01); *A61B 1/00105* (2013.01); *A61B 1/00135* (2013.01); *A61B 1/018* (2013.01); *A61B 10/06* (2013.01); *A61B 2017/00318* (2013.01); *A61B 2017/0034* (2013.01); *A61B 2017/0046* (2013.01); *A61B 2017/2926* (2013.01)

(58) Field of Classification Search
CPC . A61B 17/29; A61B 1/00066; A61B 1/00082; A61B 1/00105; A61B 1/00135; A61B 1/018; A61B 10/06; A61B 2017/00318; A61B 2017/0034; A61B 2017/0046; A61B 2017/2926
See application file for complete search history.

(56) References Cited

U.S. PATENT DOCUMENTS

| | | | | |
|---|---|---|---|---|
| 5,167,239 A | * | 12/1992 | Cohen | A61M 25/09 604/908 |
| 5,364,365 A | * | 11/1994 | Wortrich | A61B 17/3496 604/164.12 |
| 5,370,647 A | * | 12/1994 | Graber | A61B 17/00234 606/127 |
| 5,776,097 A | * | 7/1998 | Massoud | A61B 17/12186 606/192 |
| 5,779,688 A | * | 7/1998 | Imran | A61M 25/0097 604/533 |
| 5,910,105 A | * | 6/1999 | Swain | A61B 17/062 606/139 |

(Continued)

*Primary Examiner* — Anh Tuan T Nguyen
*Assistant Examiner* — Shankar Raj Ghimire
(74) *Attorney, Agent, or Firm* — Inskeep IP Group, Inc.

(57) ABSTRACT

Various devices and methods having detachable handles at a proximal end thereof for use in the working channel of an endoscope. The detachable components at the proximal end allow the endoscope to be retracted and removed over the device, while leaving the device in place for purposes such as tissue manipulation.

8 Claims, 23 Drawing Sheets

(56) References Cited

U.S. PATENT DOCUMENTS

| | | | | |
|---|---|---|---|---|
| 5,922,001 A * | 7/1999 | Yoon | A61B 17/3417 | 606/205 |
| 5,931,849 A * | 8/1999 | Desvignes | A61B 17/29 | 606/174 |
| 6,053,934 A * | 4/2000 | Andrews | A61B 17/2909 | 600/104 |
| 6,074,408 A * | 6/2000 | Freeman | A61B 17/29 | 606/205 |
| 6,077,290 A * | 6/2000 | Marini | A61B 17/29 | 606/174 |
| 6,221,007 B1 * | 4/2001 | Green | A61B 1/00052 | 600/106 |
| 6,234,996 B1 * | 5/2001 | Bagaoisan | A61M 5/31586 | 604/99.01 |
| 6,544,276 B1 * | 4/2003 | Azizi | A61B 17/12036 | 604/528 |
| 6,764,499 B2 * | 7/2004 | Honey | A61B 17/2909 | 606/127 |
| 8,328,837 B2 * | 12/2012 | Binmoeller | A61M 25/104 | 604/164.01 |
| 10,136,881 B2 * | 11/2018 | Mariani | A61B 17/0218 | |
| 2002/0091394 A1 | 7/2002 | Reynolds | A61B 17/00234 | 606/127 |
| 2004/0138701 A1 * | 7/2004 | Haluck | A61B 17/29 | 606/205 |
| 2005/0113716 A1 * | 5/2005 | Mueller | A61B 10/0041 | 600/568 |
| 2005/0209612 A1 * | 9/2005 | Nakao | A61B 17/062 | 606/144 |
| 2005/0261674 A1 * | 11/2005 | Nobis | A61B 1/012 | 606/45 |
| 2005/0272977 A1 * | 12/2005 | Saadat | A61B 1/04 | 600/114 |
| 2006/0036277 A1 * | 2/2006 | Kieturakis | A61M 25/0668 | 606/192 |
| 2006/0189845 A1 * | 8/2006 | Maahs | A61B 1/04 | 600/146 |
| 2006/0247720 A1 * | 11/2006 | Starkebaum | A61B 5/6882 | 607/40 |
| 2007/0016172 A1 * | 1/2007 | Charukhchian | A61J 15/0019 | 604/326 |
| 2007/0293724 A1 * | 12/2007 | Saadat | A61B 1/015 | 600/156 |
| 2008/0262293 A1 * | 10/2008 | Murakami | A61B 90/50 | 600/101 |
| 2009/0030380 A1 * | 1/2009 | Binmoeller | A61M 25/104 | 604/509 |
| 2009/0171147 A1 * | 7/2009 | Lee | A61B 17/29 | 600/137 |
| 2010/0042107 A1 * | 2/2010 | Merrifield | A61B 17/221 | 606/127 |
| 2010/0228085 A1 * | 9/2010 | Mirza | A61B 17/320016 | 600/114 |
| 2011/0112517 A1 * | 5/2011 | Peine | A61B 17/2909 | 606/1 |
| 2011/0172491 A1 * | 7/2011 | Piskun | A61M 39/26 | 600/104 |
| 2012/0078118 A1 * | 3/2012 | Jenkins | A61B 17/24 | 600/478 |
| 2012/0116394 A1 * | 5/2012 | Timm | A61B 17/320092 | 606/41 |
| 2012/0150063 A1 * | 6/2012 | Rea | A61B 5/296 | 600/554 |
| 2013/0096378 A1 * | 4/2013 | Alexander | A61B 1/00114 | 606/191 |
| 2013/0211196 A1 * | 8/2013 | Belson | A61B 17/0469 | 606/1 |
| 2014/0107690 A1 * | 4/2014 | Ishii | A61B 17/29 | 606/205 |
| 2014/0236064 A1 * | 8/2014 | Binmoeller | A61B 17/1114 | 604/8 |
| 2015/0032119 A1 * | 1/2015 | Kuroda | A61B 17/295 | 606/113 |
| 2015/0133951 A1 * | 5/2015 | Seifert | A61N 1/0504 | 607/116 |
| 2015/0230699 A1 * | 8/2015 | Berul | A61B 1/05 | 600/104 |
| 2015/0257758 A1 * | 9/2015 | Qadeer | A61B 17/0644 | 606/219 |
| 2016/0074055 A1 * | 3/2016 | Ravikumar | A61B 17/3496 | 606/170 |
| 2016/0249919 A1 * | 9/2016 | Savage | H01M 50/20 | 227/175.1 |
| 2016/0262764 A1 * | 9/2016 | Gokharu | A61B 17/1285 | |
| 2017/0105607 A1 * | 4/2017 | Truckai | A61B 18/149 | |
| 2017/0128071 A1 * | 5/2017 | Holsten | A61B 17/068 | |
| 2017/0135749 A1 * | 5/2017 | Cagle | A61B 18/1445 | |
| 2017/0231474 A1 * | 8/2017 | Saadat | A61B 1/00087 | 600/107 |
| 2017/0238936 A1 * | 8/2017 | Mujawar | A61B 17/1285 | |
| 2017/0252057 A1 * | 9/2017 | Bonnette | A61M 25/09 | |
| 2018/0008276 A1 * | 1/2018 | Bhatnagar | A61B 17/105 | |
| 2018/0008277 A1 * | 1/2018 | Baril | A61B 17/1285 | |
| 2018/0117261 A1 * | 5/2018 | Steese-Bradley | A61M 5/2448 | |
| 2018/0161036 A1 * | 6/2018 | Merrifield | A61B 17/1285 | |
| 2018/0303498 A1 * | 10/2018 | Galdonik | A61B 17/2909 | |
| 2019/0175176 A1 * | 6/2019 | Zammataro | A61B 17/105 | |
| 2019/0365415 A1 * | 12/2019 | Haribhakti | A61B 1/07 | |
| 2020/0037863 A1 * | 2/2020 | Harris | A61B 1/0008 | |
| 2020/0038043 A1 * | 2/2020 | Motai | A61B 1/00137 | |
| 2020/0046334 A1 * | 2/2020 | Hu | A61B 17/1285 | |
| 2020/0261095 A1 * | 8/2020 | Yi | A61B 17/1285 | |
| 2021/0085153 A1 * | 3/2021 | Chu | A61B 1/00098 | |
| 2021/0100429 A1 * | 4/2021 | Chu | A61B 1/0057 | |
| 2021/0386411 A1 * | 12/2021 | Iqbal | A61B 1/00096 | |
| 2022/0015787 A1 * | 1/2022 | Schembre | A61B 10/06 | |
| 2022/0192471 A1 * | 6/2022 | Levy | A61B 1/0615 | |

* cited by examiner

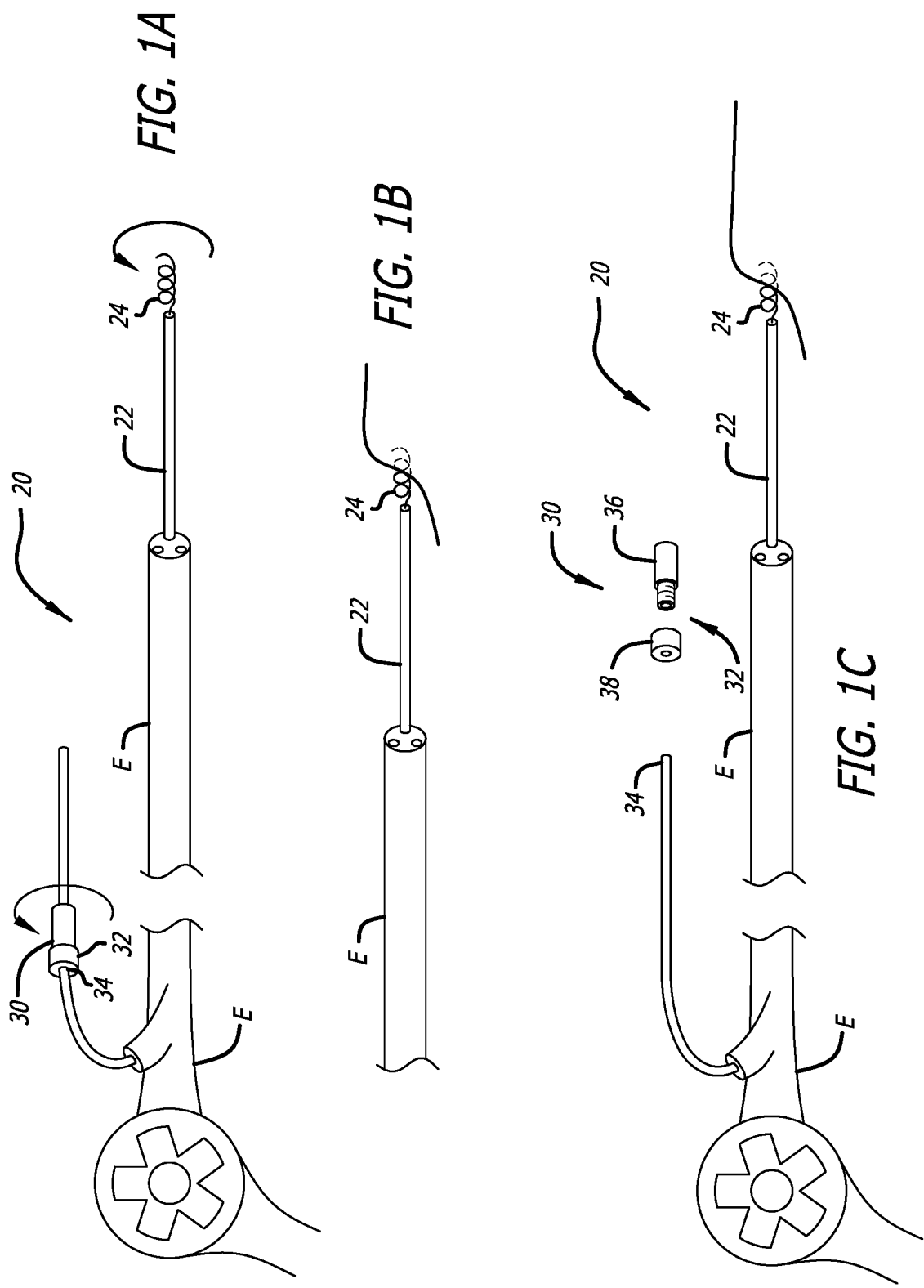

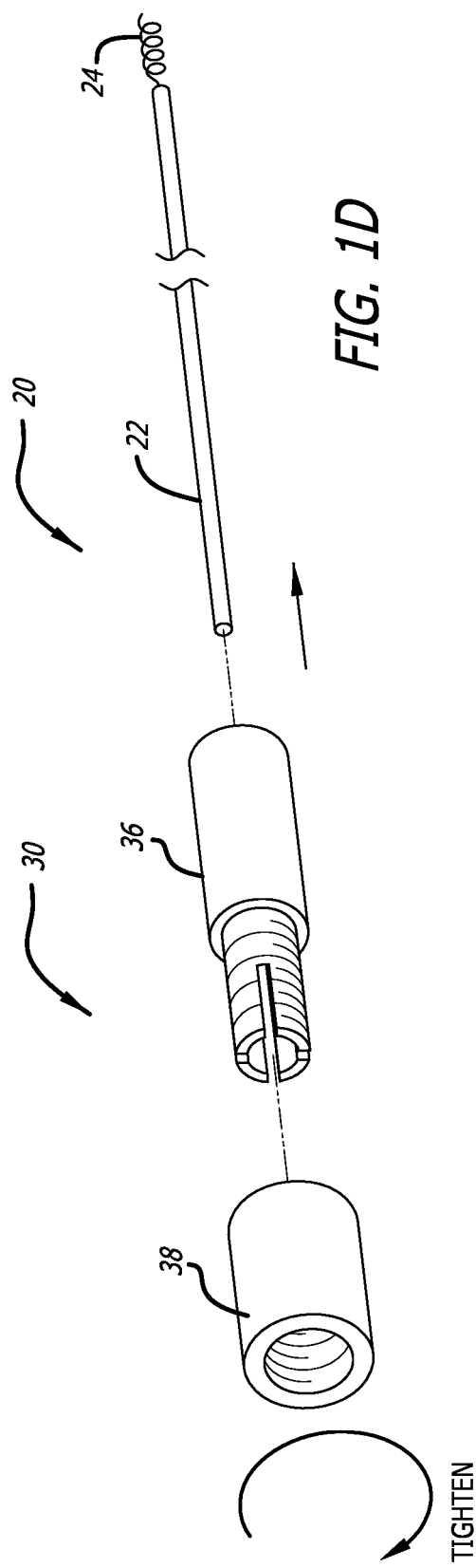
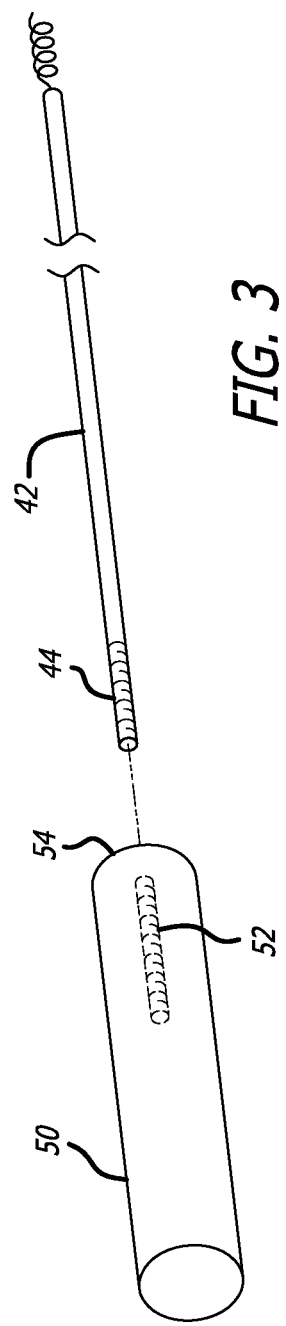

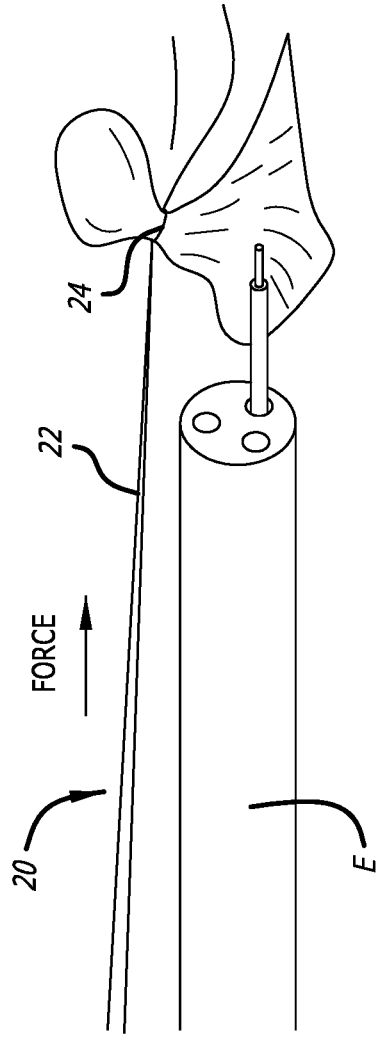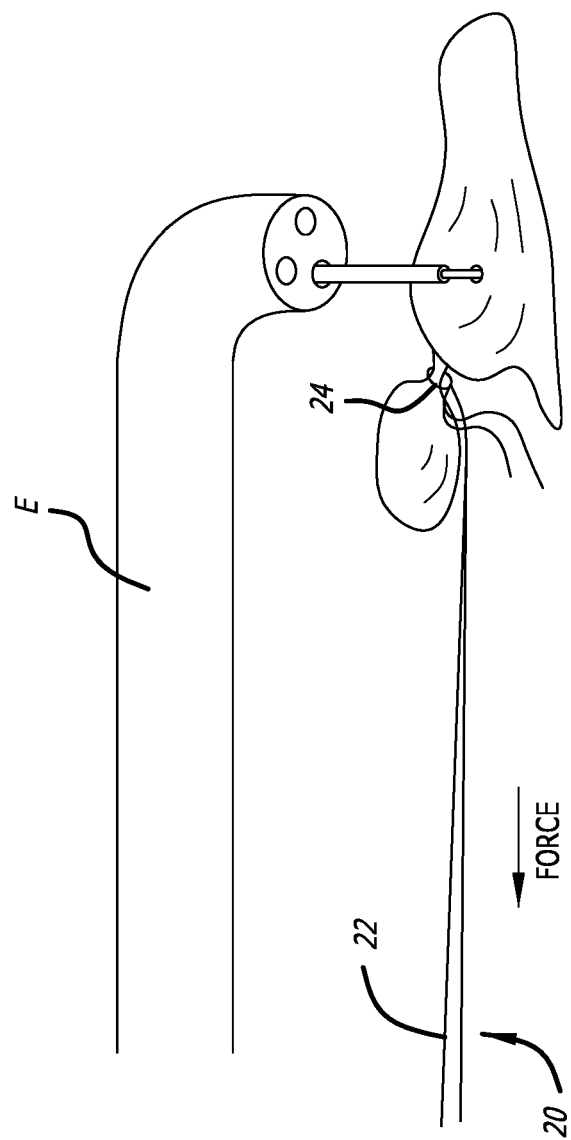

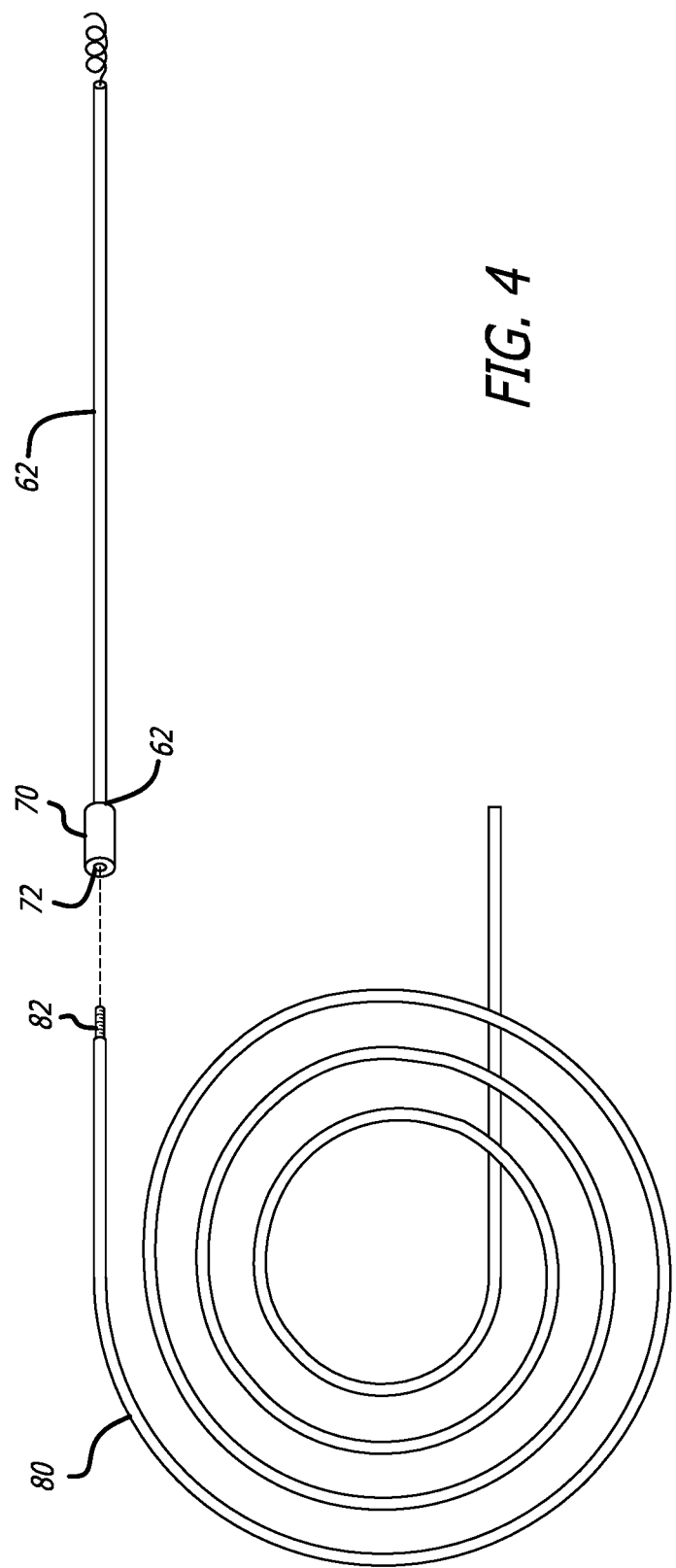

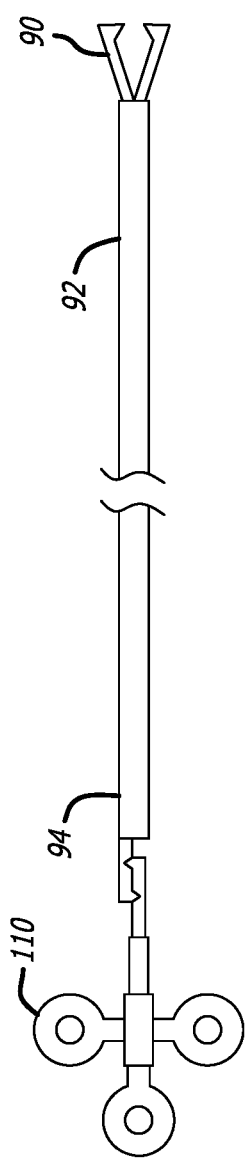
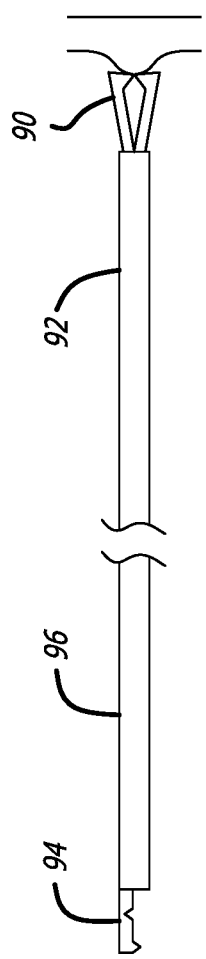
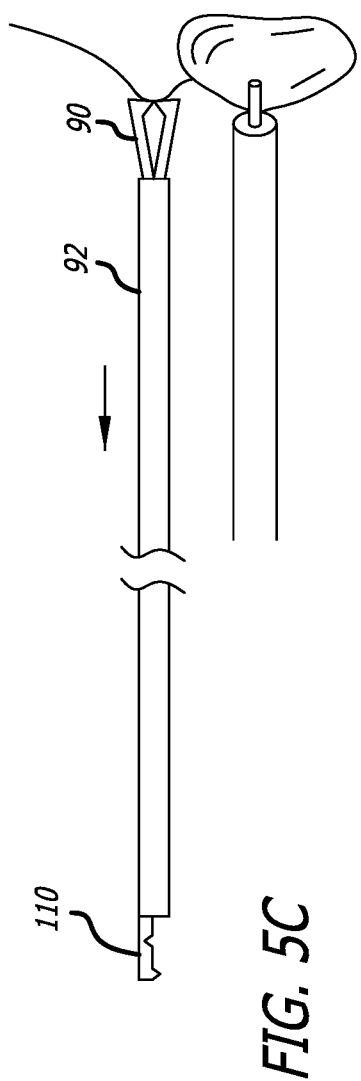
FIG. 5A
FIG. 5B
FIG. 5C

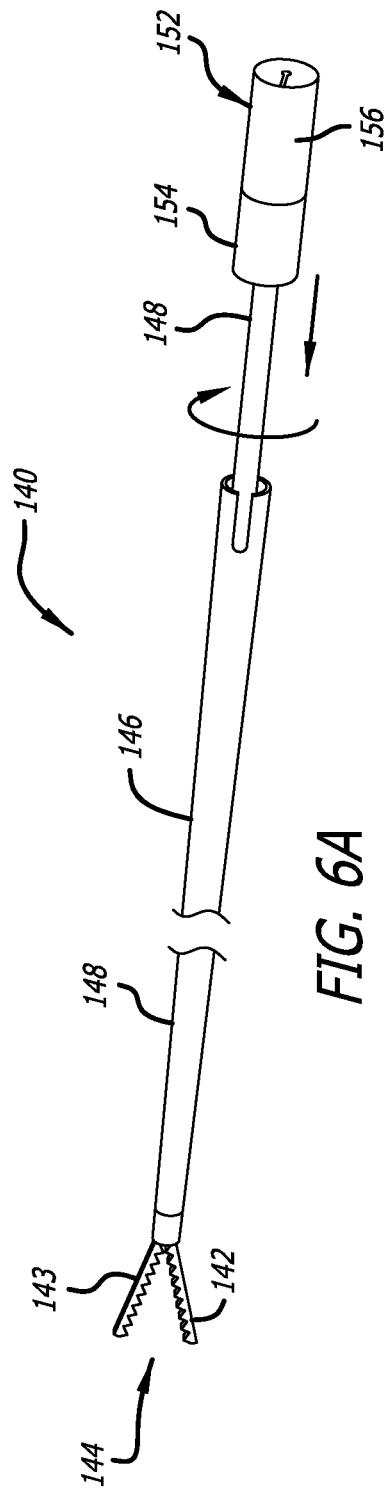
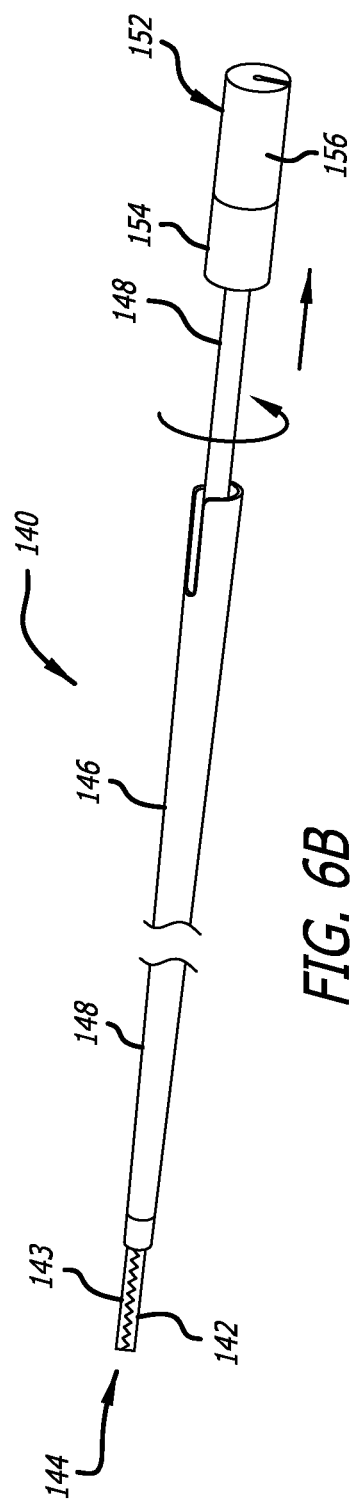
FIG. 6A
FIG. 6B

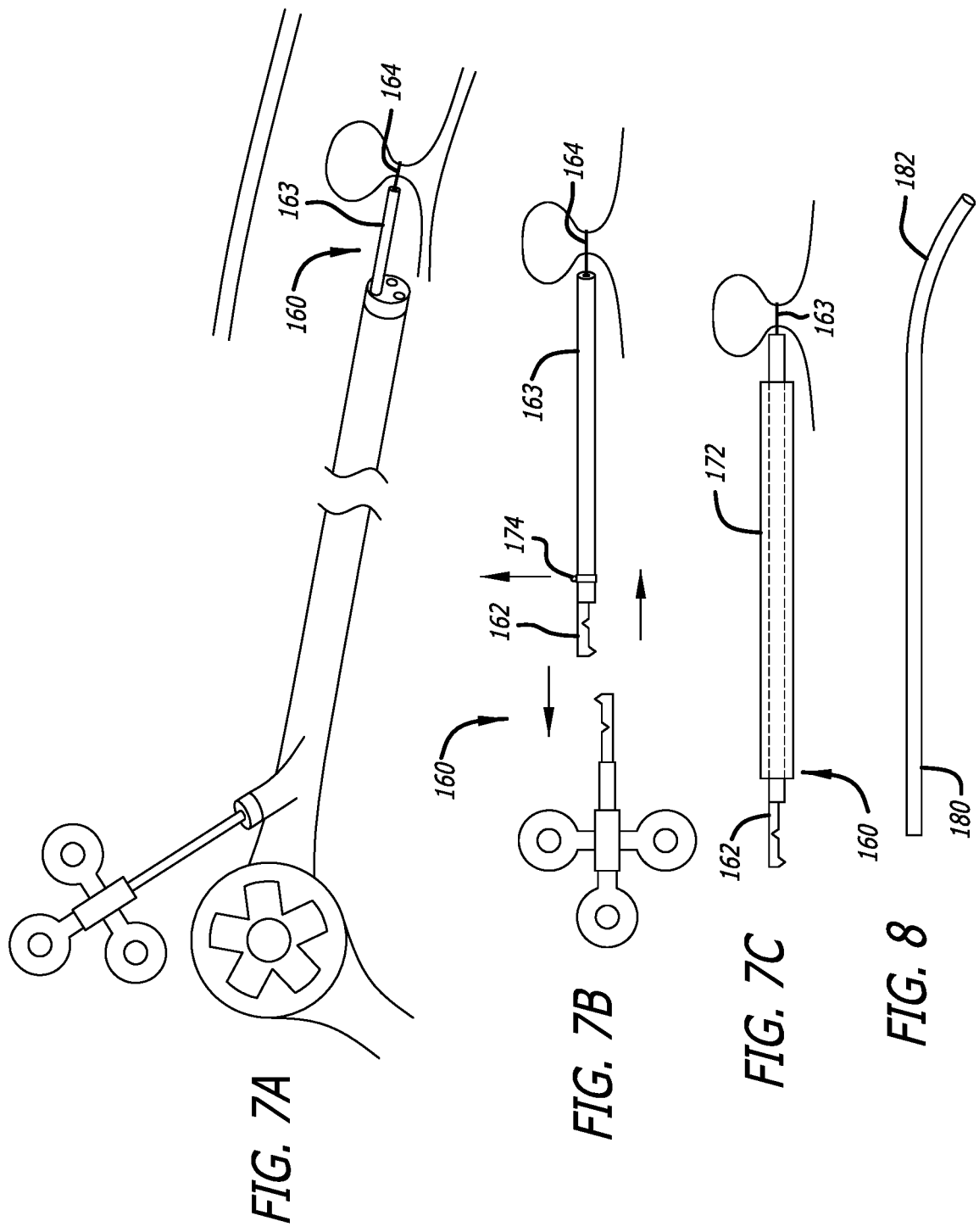

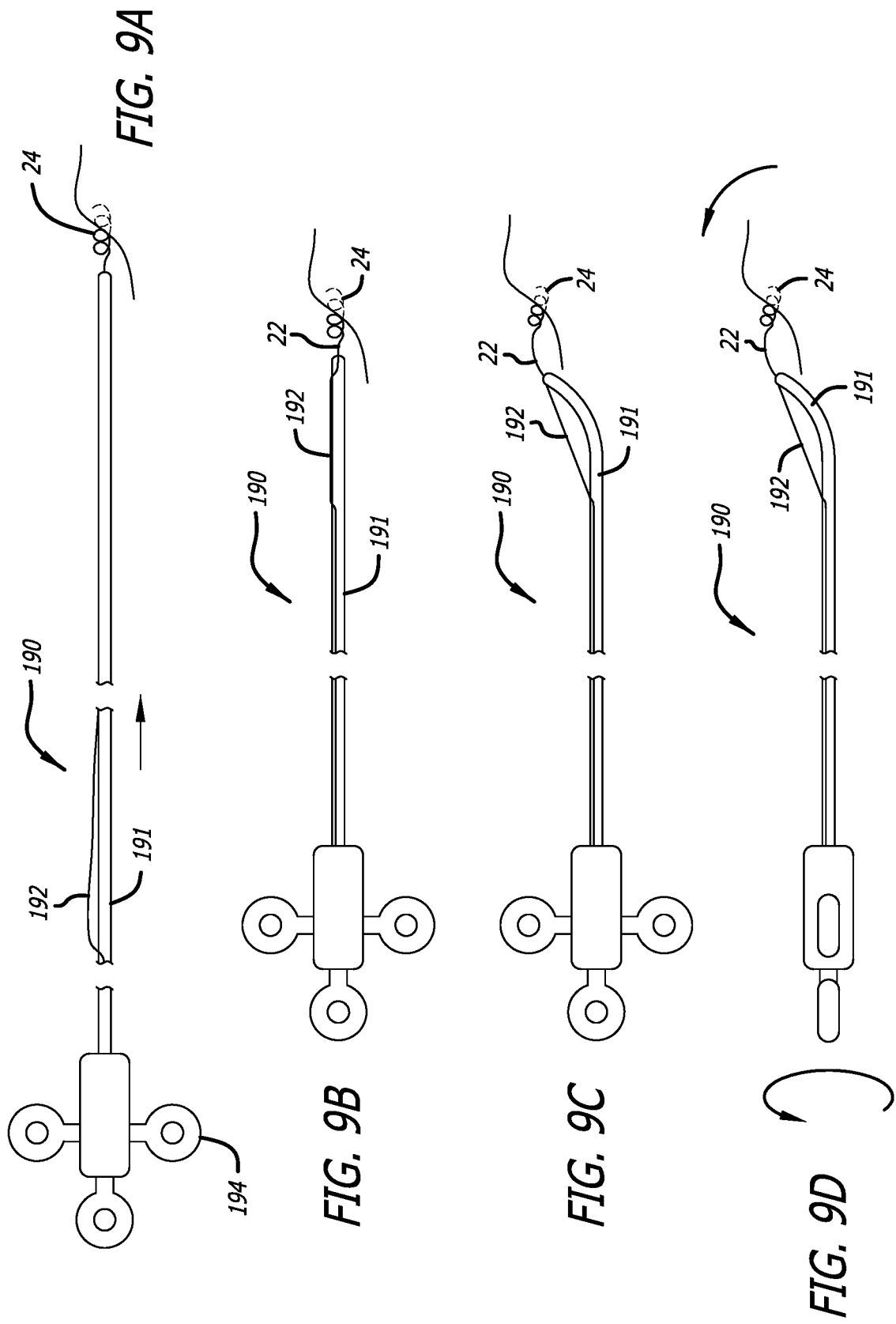

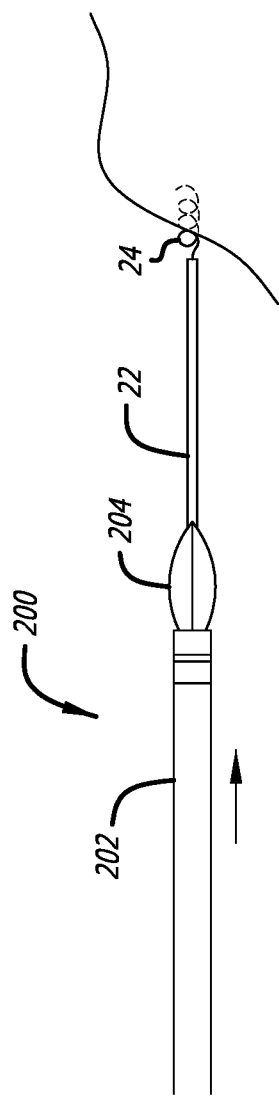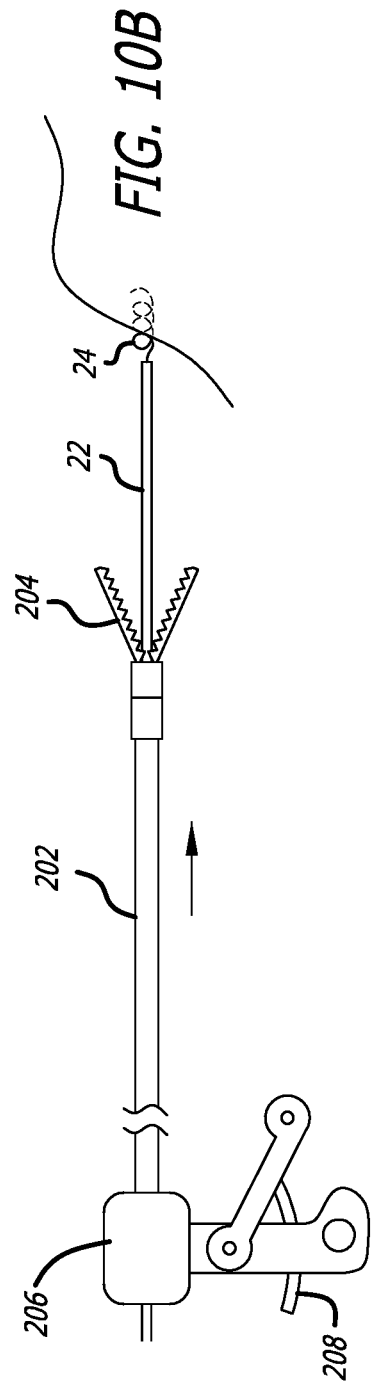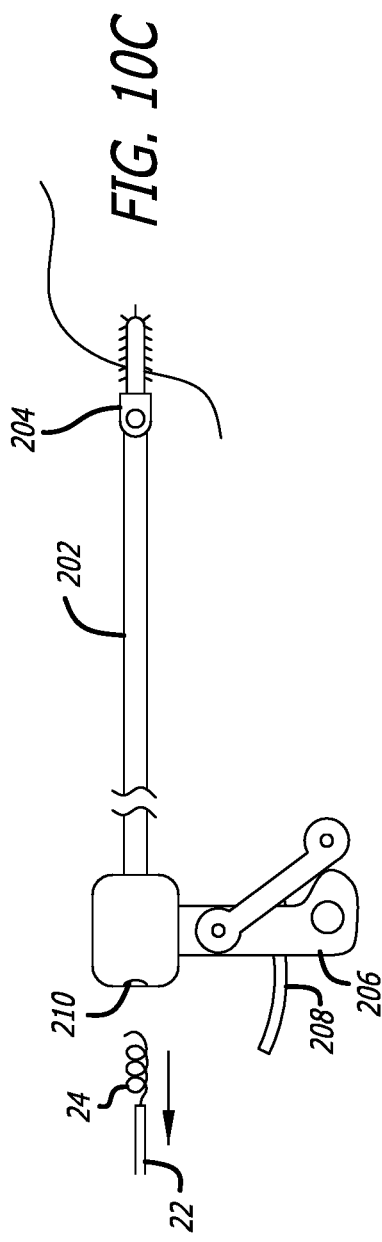

GRASPING DEVICE FOR INDEPENDENT TISSUE MANIPULATION DURING GASTROINTESTINAL ENDOSCOPIC PROCEDURES AND METHODS OF USE

RELATED APPLICATIONS

This application claims priority to U.S. Provisional Application Ser. No. 63/052,464 filed Jul. 16, 2020 entitled Grasping Device For Independent Tissue Manipulation During Gastrointestinal Endoscopic Procedures which is hereby incorporated herein by reference in its entirety.

BACKGROUND OF THE INVENTION

Flexible medical endoscopy allows entry, inspection and intervention into the body via natural openings such as the mouth, anus, vagina, urethra and nasal passages. The majority of interventional procedures performed via flexible endoscopy occur in the gastrointestinal tract, in part because of the relatively large entry points but also because of the great variety of conditions and organs that can be accessed. Gastrointestinal endoscopy has evolved from a strictly diagnostic tool to a platform for complex therapeutic procedures including tissue resection, defect closure and even volume reduction bariatric procedures. However, unlike minimally invasive techniques such as laparoscopic surgery, flexible endoscopy relies on a single point of access and a limited "one handed" mechanism for performing procedures. Despite over 50 years of technological advances, the vast majority of flexible endoscopic interventions are still performed through a single, small working channel. Despite great advances in the devices used through this port, almost all consist of a single tool, limited both by their ability to pass through the channel and by the degrees of freedom afforded by the movement of the endoscope. Ultimately, procedures through the flexible endoscope equate to performing a task with one hand; there is no real ability to hold or manipulate a target independent of the actions of the single device passed through the endoscope. Even with double or multi-channel instruments, the passage through the same endoscope severely limits independent motion. This platform restricts complex movement and tissue manipulation and precludes effective counter-traction and triangulation. As a result, complex work-arounds and difficult and risky techniques have been developed for some complex endoscopic procedures A variety of techniques have been developed to compensate for limitations associated with a single device channel. These include multi-channel endoscopes and the endoscopic placement of other devices, such as externally controlled magnets, spring-loaded clips, and clips with suture or dental floss tethers. Multichannel endoscopes are large and at times difficult to maneuver and devices passed through separate channels still operate in the same plane. Magnets and suture-manipulated clips are unwieldy and have not gained widespread use.

Tissue graspers currently exist for flexible endoscopy. Most are comprised of movable jaws that are activated by wires via an actuator handle at the proximal endo of the working channel, outside the body and the endoscope. A rotational helix-type tissue acquisition device has been incorporated into complex endoscopic tools such as an endoluminal plicator (Esophyx, Endogastric Solutions, Redmond, WA) and an endoscopic suturing platform (Overstich, Apollo Endosurgery, Inc, Austin Tx). Both platforms incorporate the tissue grasper within a fixed channels of the endoscope or associated overtubes.

Examples of these devices and methods may be found at https://www.overstitch.com/ and https://www.endogastricsolutions.com.

A handful of devices have been developed that allow the endoscope to be removed with the device still in place. The most notable is the naso-biliary/cystic drain. (https://www.cookmedical.com/products/esc_enbd_webds/) This is a long drainage tube that can be placed in the gallbladder or in a peri-luminal cavity via an endoscope and left in place as the scope is withdrawn. It allows flushing and drainage that can only be accomplished by placing a Luer-lock adapter on the catheter after it has been pulled through the endoscope channel.

There is thus a need for a tool design that allows a variety of tools to be delivered through the working channel of an endoscope, which allow the endoscope to be removed while leaving the tool in place. The endoscope can then be reinserted and used to view the distal end of the tool from a variety of angles and perspectives. The working channel of the endoscope could then be used to introduce a second tool, if desired.

OBJECTS AND SUMMARY OF THE INVENTION

In order to address the identified need, the various embodiments of the invention are directed toward a tool design that includes a detachable proximal tool handle that, when detached proximal of an endoscope working channel port, leaves a connector that is small enough to pass through the working channel of the endoscope as the endoscope is being withdrawn from the patient, thus leaving the tool in place and allowing the tool handle to be reattached.

One or more embodiments of the invention are directed toward a tissue grasping device that can be placed endoscopically and left connect to the tissue while disengaged from the endoscope by removing the control handle and sliding the endoscope out of the body while the grasper remains attached to the target tissue. The endoscope can then re-enter the body alongside the grasper to visualize and engage with the target tissue. The target tissue can then be "pulled" proximally or "pushed" distally by exerting ether traction or forward pressure, respectively, on the grasper, independent of the endoscope or any subsequent devices passed through the endoscope. This allows for independent, axial movement. Passage of subsequent catheters with additional functionality over this anchor grasper will add additional control and directionality that can enable greater controlled movement in additional planes.

One aspect of the invention provides a distal end with an anchoring feature that allows the tool to be attached to tissue such that when the endoscope is withdrawn, the distal end of the tool remains in a desired location.

In one or more embodiments, the anchoring feature comprises a helical corkscrew design.

In one or more embodiments, the anchoring feature comprises a clamp.

In one or more embodiments, the anchoring feature comprises jaws.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1A is a perspective view of an embodiment of a device of the invention being used with an endoscope;

FIG. 1B is a perspective view of an embodiment of a device of the invention being used with an endoscope;

FIG. 1C is a perspective view of an embodiment of a device of the invention being used with an endoscope;

FIG. 1D is a perspective view of an embodiment of a device of the invention;

FIG. 2E is a step of an embodiment of a method of the invention;

FIG. 2F is a step of an embodiment of a method of the invention;

FIG. 3 is a perspective view of an embodiment of a device of the invention;

FIG. 4 is a perspective view of an embodiment of a device of the invention;

FIG. 5A is a perspective view of an embodiment of a device of the invention;

FIG. 5B is a perspective view of an embodiment of a device of the invention;

FIG. 5C is a perspective view of an embodiment of a device of the invention;

FIG. 6A is a perspective view of an embodiment of a device of the invention;

FIG. 6B is a perspective view of an embodiment of a device of the invention;

FIG. 7A is a perspective view of an embodiment of a device of the invention being used with an endoscope;

FIG. 7B is a perspective view of an embodiment of a device of the invention;

FIG. 7C is a perspective view of an embodiment of a device of the invention;

FIG. 8 is a perspective view of an embodiment of a device of the invention;

FIG. 9A is a perspective view of an embodiment of a device of the invention;

FIG. 9B is a perspective view of an embodiment of a device of the invention;

FIG. 9C is a perspective view of an embodiment of a device of the invention;

FIG. 9D is a perspective view of an embodiment of a device of the invention;

FIG. 10A is a perspective view of an embodiment of a device of the invention;

FIG. 10B is a perspective view of an embodiment of a device of the invention;

FIG. 10C is a perspective view of an embodiment of a device of the invention;

DESCRIPTION OF EMBODIMENTS

Figure 2A:
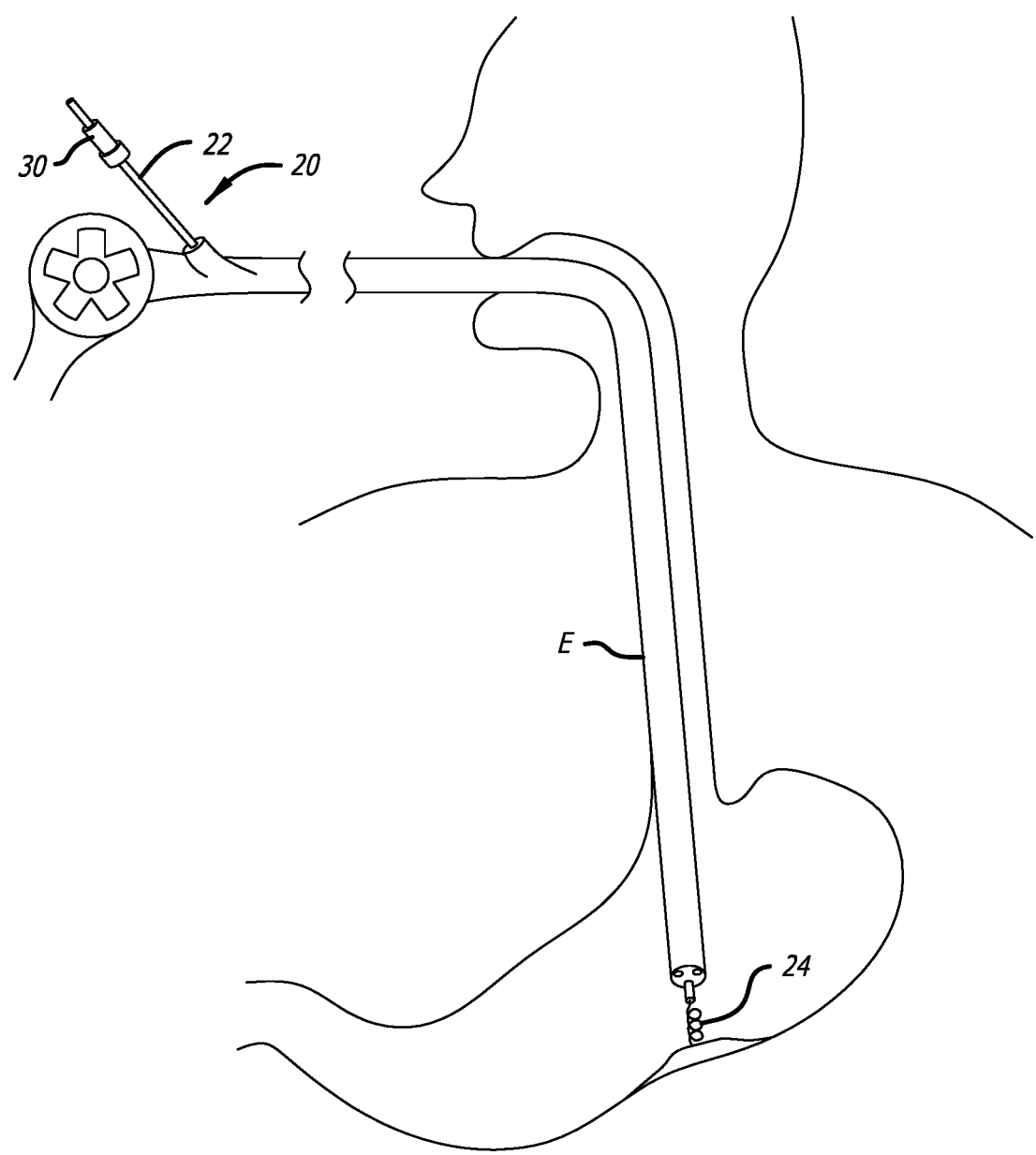
FIG. 2A is a step of an embodiment of a method of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring first to FIGS. 1A-1D, there is shown a first embodiment 20 of a grasping device that can be advanced to a target site through a working channel of an available endoscope E and left in place while the endoscope E is removed. The grasping device 20 includes a long shaft 22 with a tool 24, in this case a sharp, helical tip 24, at its distal end. The tool 24 is sized for passing through the working or accessory channel of a standard endoscope E.

The shaft 22 may be a long stainless-steel shaft or wire with partial flexibility that allows lateral flexion but is rotationally stiff enough to allow rotation at the proximal end to be translated to the distal end.

At a distal end 23 of the shaft 22 is located the helical tip 24, which may be varied in length depending on the application. For example, if the device is to be used gastrointestinally, the tip 24 should be selected to approximate the thickness of normal human gastrointestinal luminal tissue. Thus, when rotated the tip 24 should penetrate the mucosa and submucosa and possibly a portion of muscularis propria but not be long enough to penetrate serosa or pass through the full thickness of the organ.

At a proximal end 34 of the shaft 22, the device 20 has a detachable handle 30. The handle 30 is useable for rotating the helical tip 24 to capture tissue to a limited and/or predetermined depth by penetrating the tissue as indicated with the arrow in FIG. 1A. In at least one embodiment, tissue may be collected on the helix as the helix is screwed into the tissue.

The detachable handle 30 has a mechanism 32 at its distal end 34 that attaches to the proximal end 26 of the device. The mechanism 32 includes an inner collet 36 and an outer sleeve 38 that tightens the collet 36 around the shaft 22 when the mechanism is placed over the shaft 22 and the sleeve 38 is advanced over the collet 36. The separate components are shown separated in FIG. 1C. In this embodiment, the mechanism 32 is the combination of the inner collet 36 and the outer sleeve 38. Furthermore, when mechanism 32 is assembled, it constitutes the handle 30. The handle may comprise additional features such as grip features and the like. For example, in at least one embodiment, the outer surface of the sleeve 38 is textured, such as with ribs, knurling, etching, etc.

Additionally, the sleeve 38 is shown as being located distally (toward the endoscope E) of the collet 36 but one skilled in the art will understand that a collet squeezes radially and could be located distally of the sleeve with the same effect. FIG. 1D shows a closer view of a collet 36, a sleeve 38 and a shaft 22. In this view, the collet 36 is being placed over the shaft 22 first and the sleeve 38 is then tightened onto the collet 36. As such the sleeve 38 is proximal of the collet 36.

The use of the term "collet" is not meant to be limiting. Other mechanisms are envisioned that can be adjustably tightened around the proximal end 34 of the shaft 22 for rotational and translational control of the tool 24 at the distal end of the shaft 22. Conversely, the mechanism are also able to be adjustably loosened for removal of the handle 30 from the shaft 22.

Having described on embodiment of the invention, and prior to describing further embodiments and accessories, clarity may be further provided by describing a general method of the invention. Referring to FIGS. 2A-2F, one embodiment of a method of using the device involves providing an assembled device 20, meaning the handle 30 is assembled and attached to the shaft 22. The endoscope E is navigated to the target site and, once in position, the device is advanced until the tip 24 is engaged with tissue at a desired location, as viewed through the scope.

Figure 2B:
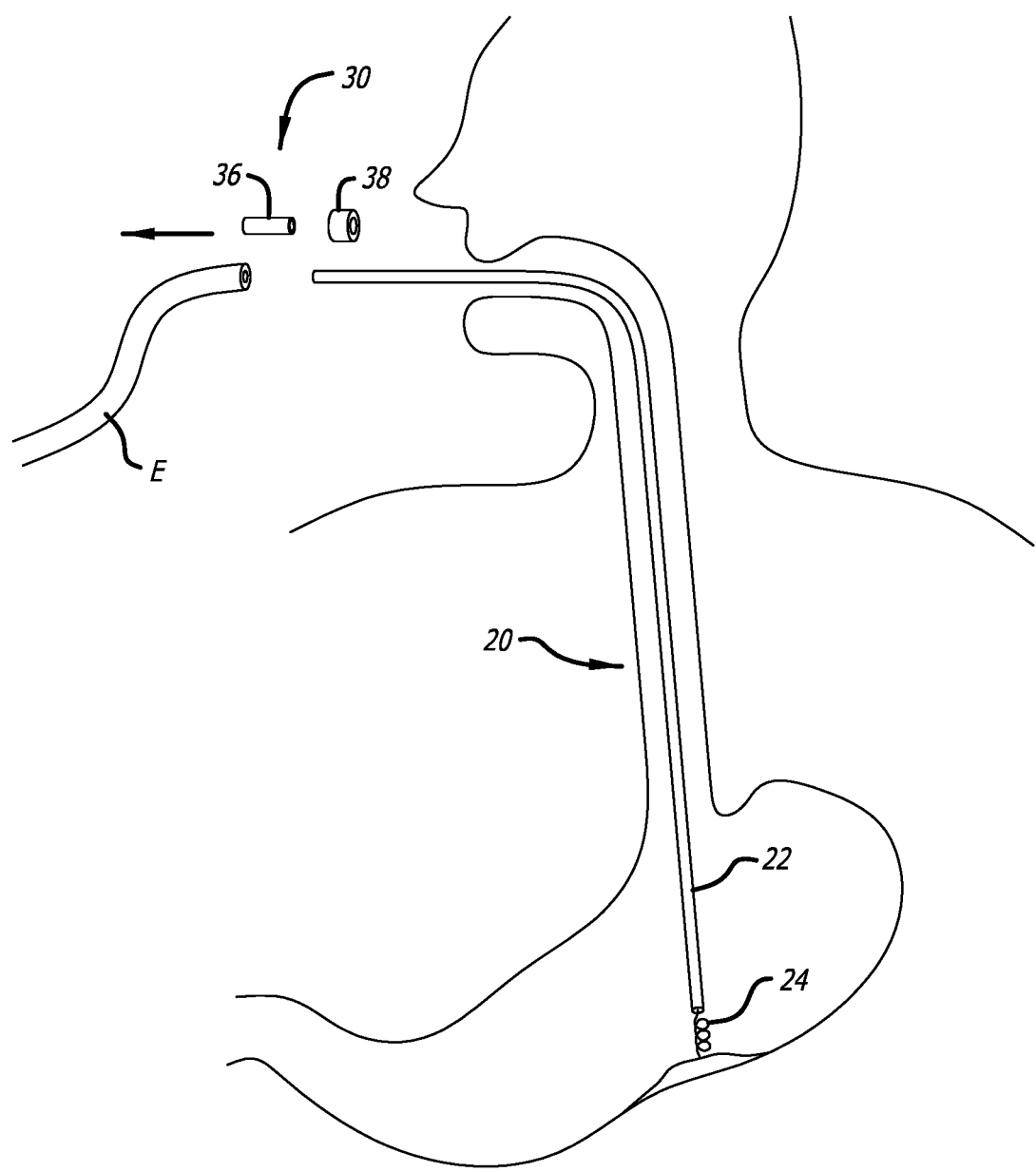
FIG. 2B is a step of an embodiment of a method of the invention.

The handle 30 is then rotated in an appropriate direction, likely clockwise according to convention, such that the helical tip 24 drives itself into the targeted tissue. The handle attaches to the shaft by passing over the shaft in a loose configuration and affixed to the shaft by tightening a sleeve over a slotted cylinder, which in turn, is compressed onto the shaft creating friction between the two surfaces, enabling 1:1 rotation of the shaft with rotation of the handle. Depth of insertion and amount of tissue capture is limited by the number of rotations and the length of the helix. As shown in FIG. 2B, once the tip 24 adequately engaged with the tissue, the handle 30 is disconnected from the shaft 22 by unscrewing the sleeve 38 from the collet 36. Once the collet 36 is loosened, the entire handle can be removed. With the handle removed, the endoscope may be retracted over the shaft 22 as the remaining portion of the device 20 is now narrow enough to pass completely through the working channel of the endoscope. As the endoscope is being retracted, the tip 24 remains anchored to the tissue, ensuring that the shaft 22 and tip 24 remain in place.

Figure 2C:
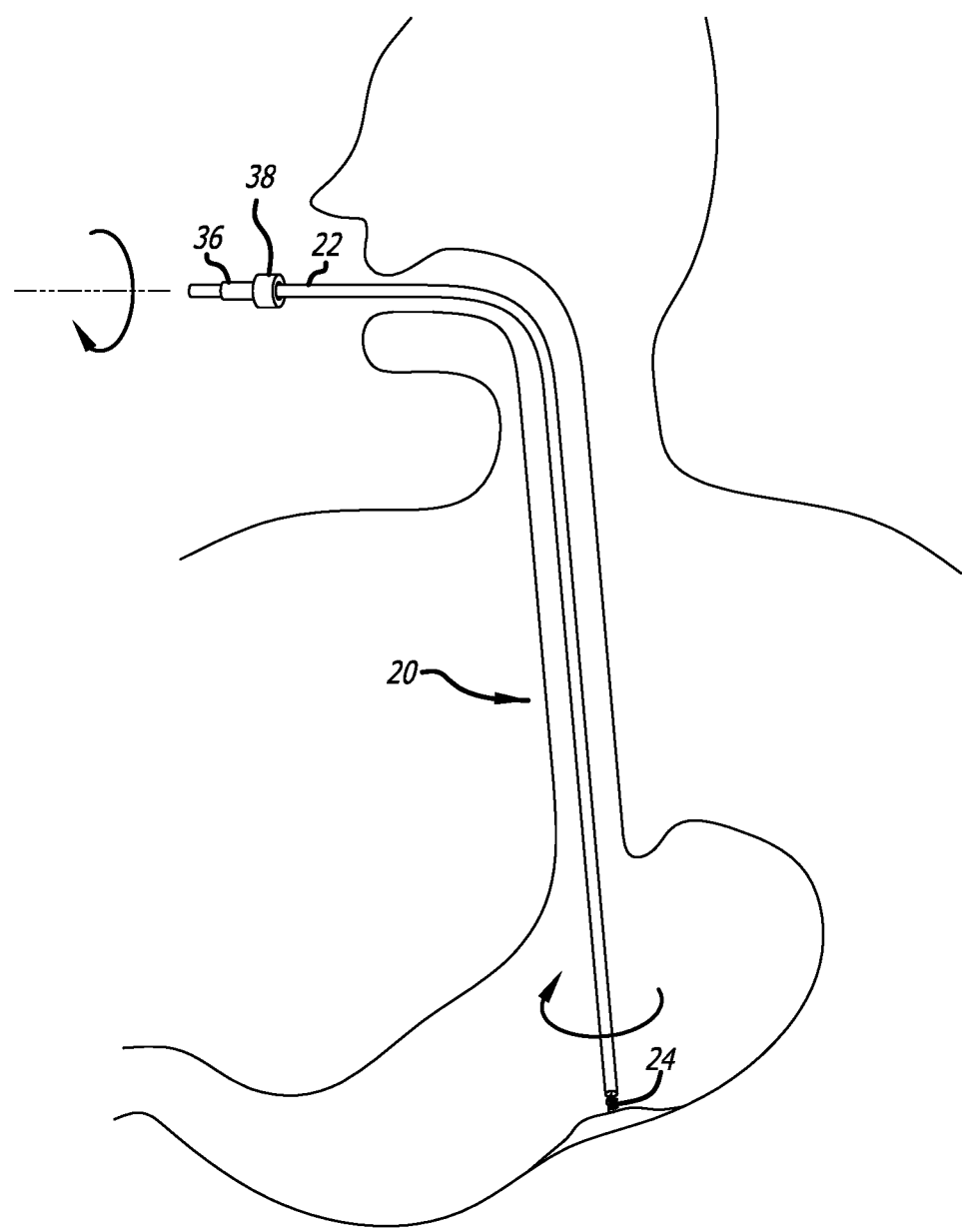
FIG. 2C is a step of an embodiment of a method of the invention.

Referring now to FIG. 2C, once the endoscope E has been removed, the handle 30 can be replaced over the shaft 22 of the device 20 and the sleeve 38 tightened. This enables easy and safe removal of the device from the target tissue via simple counterclockwise rotation, to unscrew the tip 24 from the tissue, without needing the aid of the endoscope if an emergency or therapeutic decision required its removal.

Figure 2D:
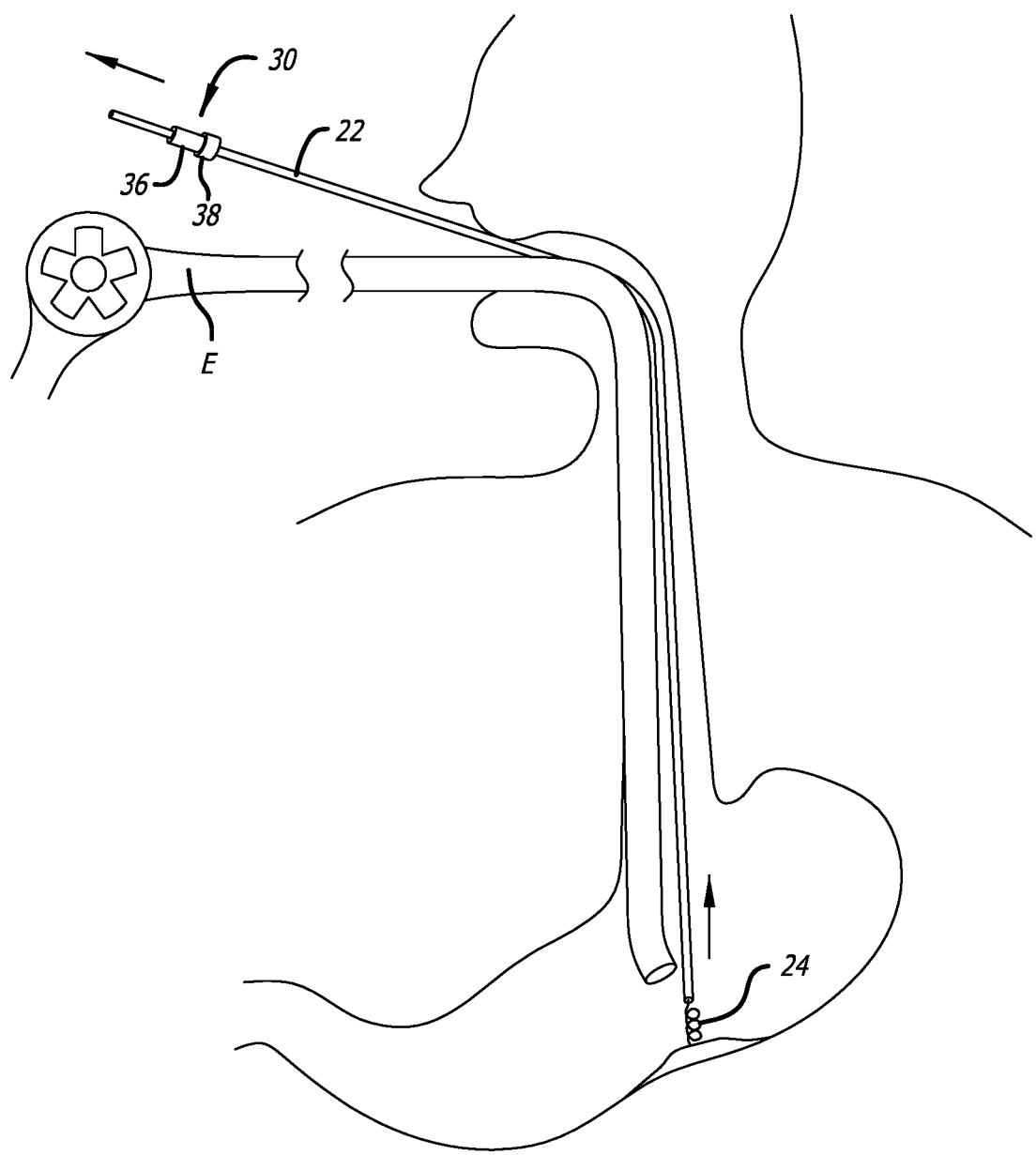
FIG. 2D is a step of an embodiment of a method of the invention.

Referring to FIG. 2D, with the device 20 in position, the endoscope E can be reinserted alongside the device 20 and the target tissue visualized from various angles. Additional tools may also be passed through the working channel of the endoscope to allow two separate tools to manipulate the tissue, while observation is made through the endoscope.

For example, as shown in FIGS. 2E and 2F, the device 20 can manipulate the target tissue in at least two directions, proximally with traction and distally by applying forward pressure, along the axis of the shaft of the device. In contrast to gaspers and other devices passed through the endoscope, this tissue movement can be completely independent of the position of the endoscope, as well as freeing up the working channel of the endoscope for other devices, such as an electrocautery knife for submucosal dissection.

FIG. 3 shows an alternative embodiment of a shaft 42 and a handle 50. The shaft 42 has a threaded proximal end 44, that is configured to mate with a threaded opening 52 at a distal end 54 of the handle 50. In this embodiment, the proximal or actuator end of the wire has no fixed attachments or adornments other than the threaded tip 44 at the most proximal end.

Despite the various anchoring devices described herein, it is desirable to ensure that, when retracting the endoscope, pulling forces are not imparted to the grasping devices. One way to accomplish this is to ensure that the grasping device is sufficiently long that the endoscope can be withdrawn completely before the proximal end of the grasper enters the channel. Thus, the device may be fed into the working channel while the endoscope is being retracted so that the feeding force being applied offsets the retracting force. Once the endoscope is removed from the patient, the grasper can be held between the distal end of the endoscope and the body opening while the endoscope is completely withdrawn over the grasping device.

It may not always be desirable to have a grasper with a length at least twice as long as an endoscope fed into patient once the endoscope is removed. As such a shorter embodiment is also provided. If the wire or shaft is bifurcated with a connecting device, a shorter grasper may be used. For example, in one embodiment, shown in FIG. 4, there is an embodiment of a shorter grasper having a shaft 62 with a threaded proximal end and a handle 70. The threaded proximal end can be connected to a complementary threaded wire of various lengths to enable controlled removal of the endoscope over the anchor shaft while affixed to target tissue in a controlled, one-to-one manner. An extension wire 80 can be removed by unscrewing it from the anchor wire once the endoscope has been completely removed.

The handle 70 is sized to pass through the working channel of an endoscope and has a female threaded opening 72 at a proximal end 64 of the shaft 62. The female threaded opening is configured to mate with a male threaded distal end 82 of the extension wire 80 by simple rotation. The extended anchor wire 80 can facilitate safe and controlled removal of the endoscope as the long wire/anchor wire complex can be passed into the endoscope as it is removed and insure that it is always under direct control of the operator until the endoscope has been removed and the wire can be grasped at the body opening. The extension wire 80 can then be removed by unscrewing it to provide a more manageable length of wire extending from the body opening.

Various embodiments of the tool at the distal end of the shafts are also provided. For example, FIGS. 5A-5C show an embodiment in which a grasper 90 that opens and closes, much like endoscopic grasper or biopsy forceps, is located at a distal end of a shaft 92. In accordance with the invention, the grasper 90 is capable of being routed through the working channel of an endoscope and operated with a removable handle 110 at the proximal end 94 of the shaft 92.

The shaft 92 passes through a sheath 96, which protects the working channel of the endoscope from the movement of the shaft 92.

As with the other embodiments, the tool, in this case the grasper 90, is capable of anchoring itself to targeted tissue and remaining anchored after the handle is removed, as shown in FIG. 5B. The grasper 90, however, anchors to tissue by clamping the tissue with the handle 110. Once clamped, a twist mechanism in the shaft enables the grasper to remain closed after the handle has been separated. A friction collar attaches the activator portion of the handle to the controlling arm of the single moveable jaw. When closed and twisted, the activating arm is locked to the fixed sheath. Once the scope has been removed, the actuator handle can be replaced without the grasper losing its grip, as shown in FIG. 5C. If an emergency occurs, the grasper 90 can be released and removed quickly.

In another embodiment, 140 shown in FIGS. 6A and 6B, there is no handle. This embodiment 140 includes a pivoting jaw 142 at a distal end of the device that pivots relative to a stationary jaw 143 to form a grasper 144. The pivoting jaw 143 is attached to a control arm 148 that resides within a sheath 146. The entire sheath 146 is thin enough to pass through the working channel of the endoscope. The pivoting jaw 142 of the grasper 144 is closed by holding the sheath 146 with one hand and pulling the control arm 148. The actuating shaft 150 of the pivoting jaw 142 then twists to lock within the sheath 146 such that the endoscope can be removed from the patient with the grasper 144 closed and holding target tissue.

Optionally, as further shown in FIGS. 6A and 6B, the device 140 may also include a detachable handle device 152 comprised of two removable cylinders 154 and 156. One of the cylinders 154 is connected to the sheath 146 (it is shown in FIGS. 6A and 6B as being separated but this is only to show the presence of the control arm 148). The second cylinder 156 is connected to the control arm 148. The two cylinders 154 and 156 may be easily grasped and translated and rotated relative to each other to effect opening and closing of the pivoting jaw 142 and locking the grasper 144 in the closed position. When tissue is captured and the shaft rotated into a locked position, the two locking cylinder handles can be removed by unscrewing the tightening collars to enable removal of the endoscope. The handle device 152 could be replaced once the endoscope has been removed to facilitate subsequent opening and closing.

Like the other embodiments described herein, the grasping device is sufficiently long that the endoscope can be withdrawn completely before the proximal end of the grasper enters the channel. At that point, the grasper can be held between the scope and the body opening while the endoscope is completely withdrawn over the grasping device. Additionally, the extension wire feature described in FIG. 4 may be used in conjunction with this and all embodiments. Thus, a shorter grasper with a threaded proximal end may be provided. Again, the threaded proximal end can be connected to a complementary threaded wire of various lengths to enable controlled removal of the endoscope over the anchor shaft while affixed to target tissue in a controlled, one to one manner. The extension wire can be removed by unscrewing it from the anchor wire once the endoscope has been completely removed.

Advantageously, all of the jaw grasper embodiments described herein can be unlocked at any time by a reverse twist to allow the control wire to pass more deeply into the sheath, thereby opening the jaw and allowing removal of the grasper from the target tissue and from the body if necessary.

The grasper could open and close exclusive of the endoscope and could re-grasp tissue under visualization by the endoscope once it has been re-positioned in the body.

Referring to FIGS. 16-20, there is shown another embodiment, 340 with a more detailed diagram of the twist-lock mechanism 350. This embodiment 340 is shown in an exploded view in FIG. 16 and includes a pivoting jaw 342 at a distal end of the device 340 that is operated by a control arm 343 that moves within a sheath 345. The device also includes a removable grip 344 and a removable actuator 346.

Figure 17:
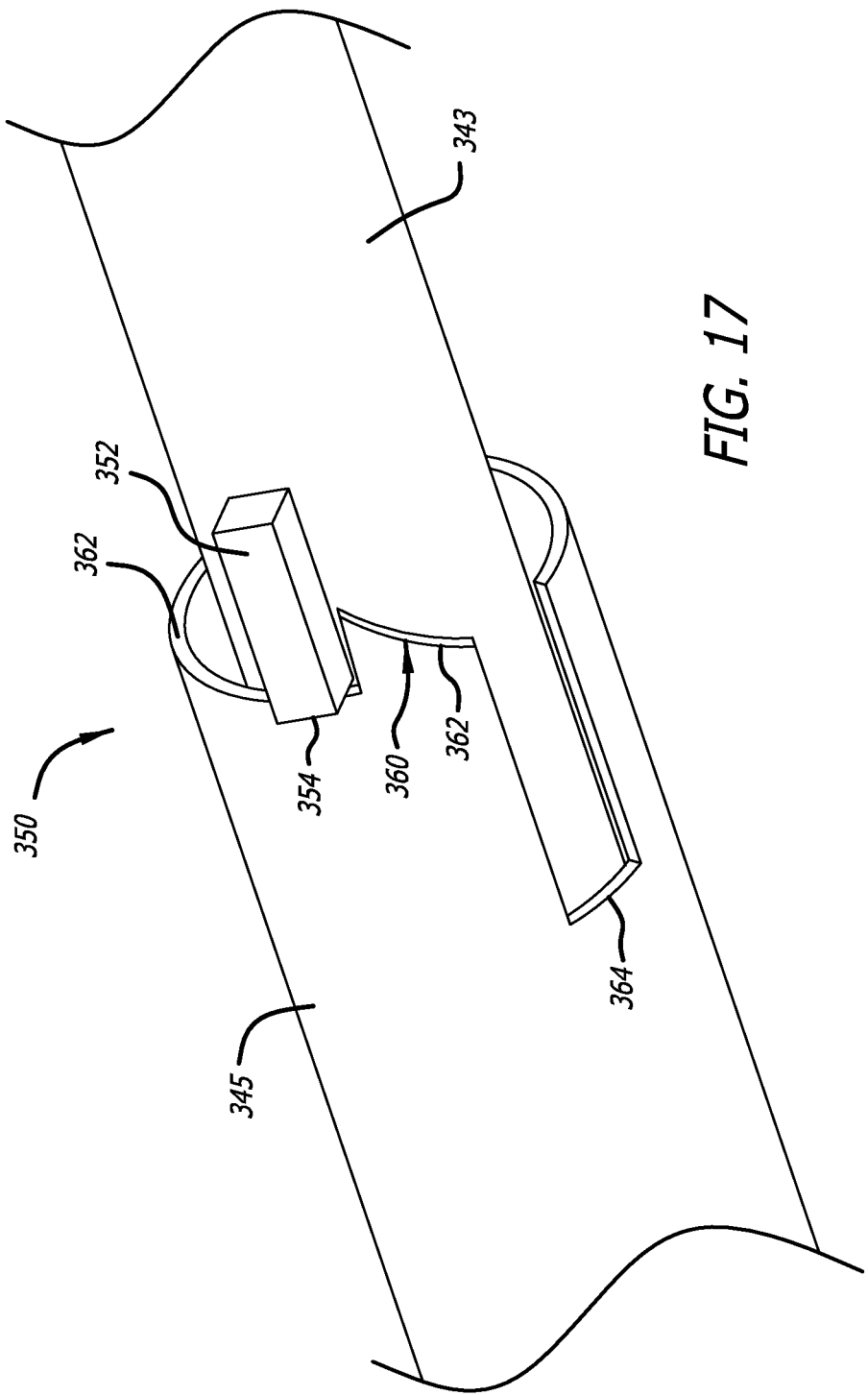
FIG. 17 is a close-up view of an embodiment of a twist lock mechanism of the invention.
Figure 18:
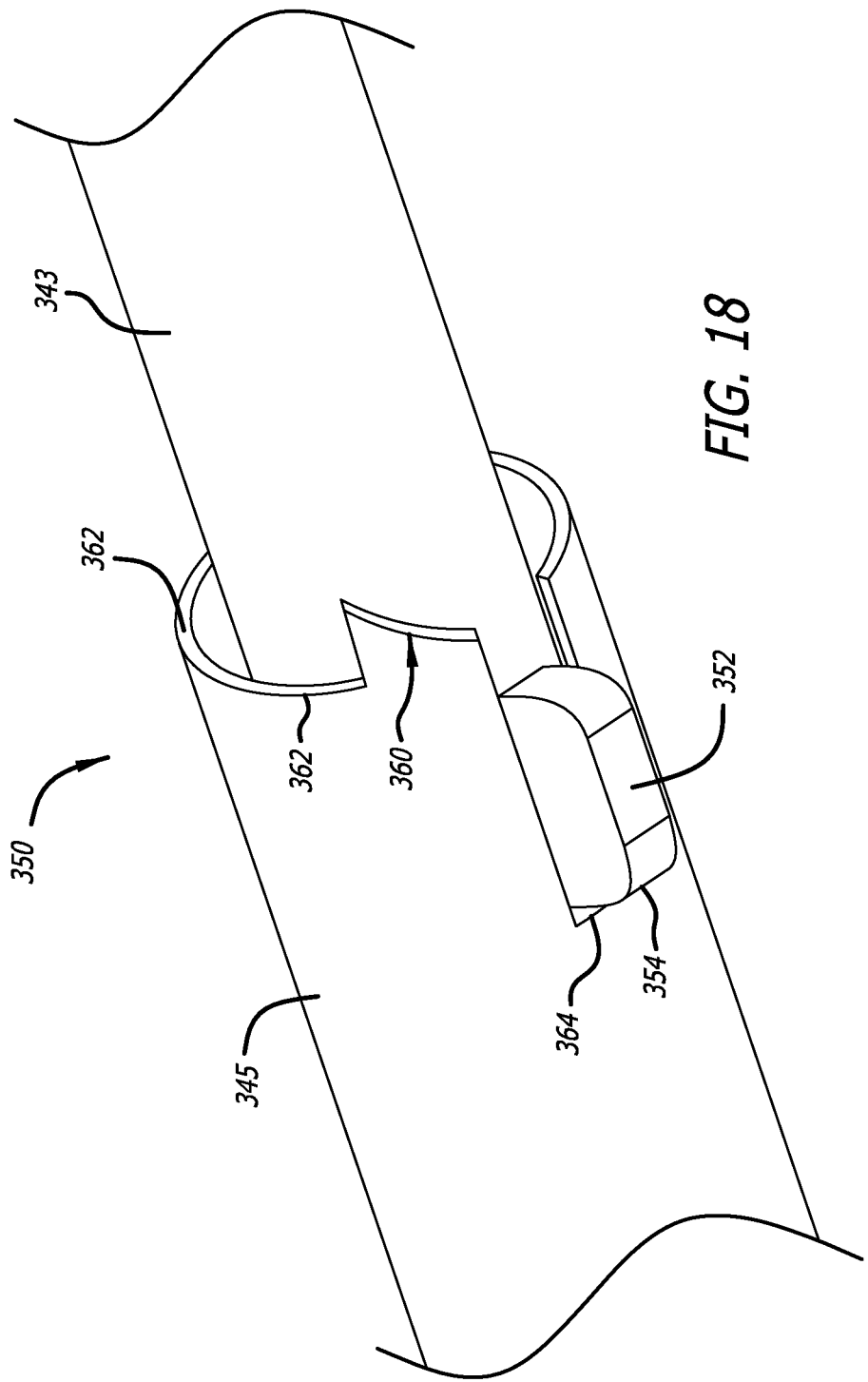
FIG. 18 is a close-up view of an embodiment of a twist lock mechanism of the invention.

Referring to FIGS. 17 and 18, the twist-lock mechanism 350 is achieved by an interaction between the control arm 343 and the sheath 345. The proximal end 360 of the control arm 343 is characterized by a plurality of angled surfaces 362 that begin and end at various longitudinal locations. Further includes is an elongated longitudinal slot 364. The sheath 345 includes a protuberance 352 with a distal edge 354 that rides along the contours of the of the angled surfaces 362.

The pivoting jaw 342 operates by pulling the control arm 343 relative to the sheath 345. Doing so closes the jaws 342. Rotating the control arm 343 relative to the sheath 345 changes the angled surface 362 with which the protuberance 352 interacts. When the protuberance 352 is aligned with the slot 364 (FIG. 18), the control arm 343 is allowed to move distally relative to the sheath 345 and the jaws 342 may open. When the protuberance 352 is aligned with any other surface 362 (FIG. 17), the jaws 342 are locked shut.

Figure 19:
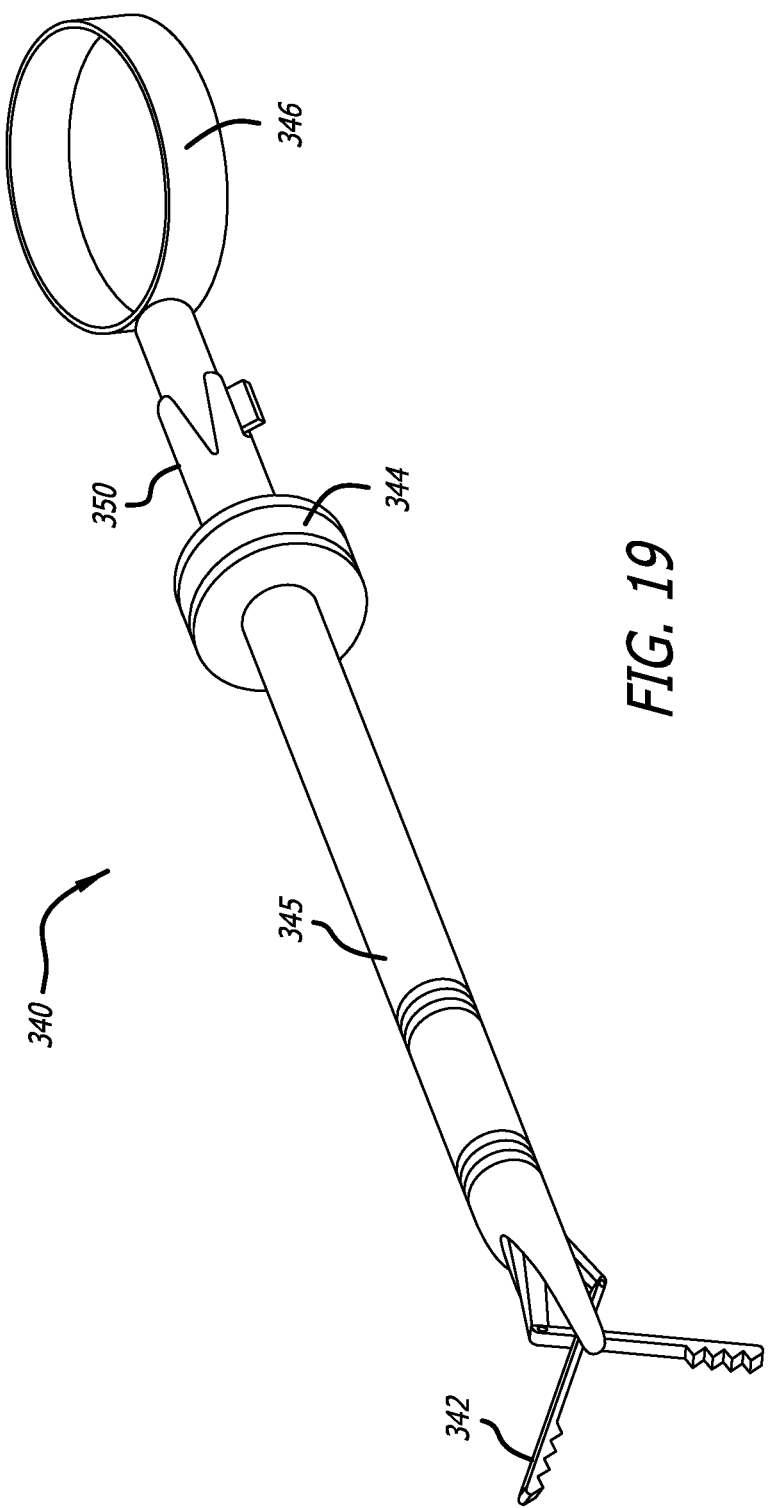
FIG. 19 is a perspective assembled view of the device of FIG. 16.
Figure 20:
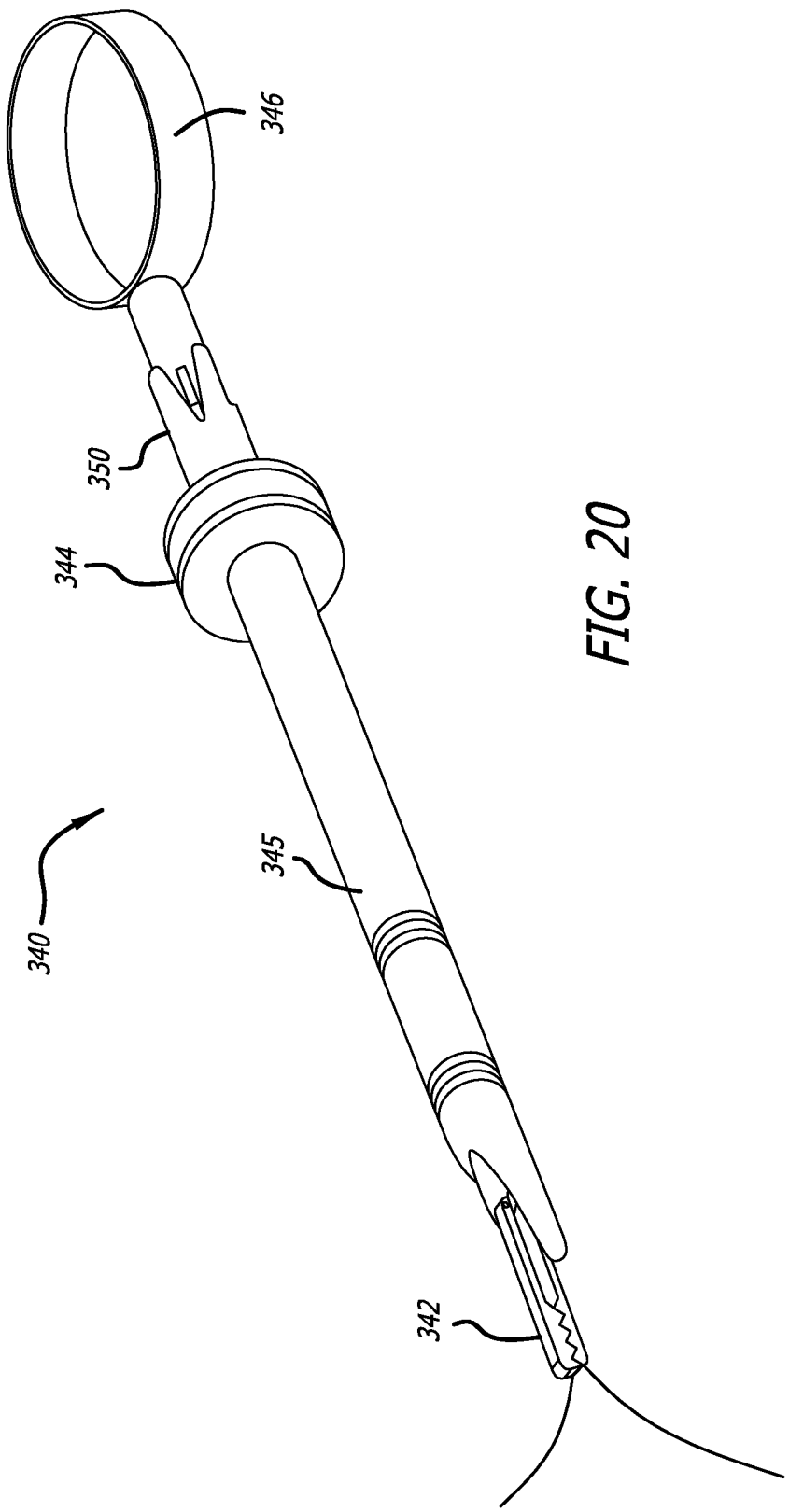
FIG. 20 is a perspective view of the device of FIG. 19 in a closed configuration; and, FIG. 21 is a perspective view of am embodiment of a device of the invention.

Operation of the device 340 is made easier by attaching the grasper 344 and the handle 346. The handle 346 is shown as having a loop that allows the handle 346 to be pulled in order to close the jaws. The grasper 344 provides a greater diameter to add torque and ease to twisting the sheath 345 and the control arm 343 relative to each other. FIGS. 19 and 20 show the device 340 fully assembled and in an open and closed configuration, respectively.

Accessory components may be provided to add different or enhanced function to the anchor devices and could be passed over the anchor wire once it was in position free of the scope. These components could provide additional properties such as rigidity, torsion or even deflection. For example, if desired, a separate sheath could pass over the grasper once the endoscope has been removed to add stiffness or other functionality to the grasper.

An embodiment of such a component is shown in FIGS. 7A-C. FIG. 7A shows a device 160 including a shaft 162 through a sheath 163 and a distal tool 164 in the form of a cinch loop. The device 160 includes a detachable handle 170 that may include any variety of finger holds to allow one-handed operation. The device 160 further includes a stiffening sheath 172 to enable better 1:1 movement forward and backward in an axial plane, (FIG. 7C). This sheath would be thicker and stiffer than the anchor wire or grasper but still flexible enough to pass over the anchor wire and accommodate to its twists and bends. Once in position, a friction sleeve could be tightened to affix the sheath to the anchor wire or grasper. Shown is a clamp 174 that can be used to affix the sheath to the shaft in this or any of the embodiments herein.

FIG. 8 shows another embodiment 180 of a sheath that has a slight "J" bend 182 at the distal tip. This sheath can be used with any of the embodiments described herein. Once the sheath has been passed over the length of the anchor wire it creates a slight bend in the anchor wire/sheath complex. Rotation of the sheath outside the body would transmit force to the anchored tissue in additional planes beyond axial, forward and back, movement.

Another embodiment 190, shown in FIGS. 9A-9D, provides an oversheath 191 with a bowing capability driven by a tensioning string or wire 192, to change the distal tip 194 to further manipulate the anchored tissue. FIG. 9A shows the oversheath embodiment 190 being used with the shaft 22 and tip 24 embodiment of FIG. 1. A handle 194 connects to both the oversheath 191 and the tensioning wire 192 such that manipulation of the handle allows the application of tension on the tensioning wire 192 relative to the oversheath 191. In use, the oversheath embodiment 190 is used to manipulate a tip or tool, such as tool 24, after the endoscope has been retracted over the device and reinserted next to the device, as described herein. The oversheath embodiment 191 is then routed over the device as seen in FIG. 9B, and used to manipulate the distal end thereof, as shown in FIG. 9C. The oversheath embodiment 191 may further include a lock, such as a twist lock 194 at its proximal end that may be used to hold the tip in a desired orientation.

Another embodiment 200 of an accessory component is seen in FIGS. 10A-C and includes an oversheath 202 with large jaws 204 at a distal end thereof. The oversheath is designed to be able to be routed over an device that is free of an endoscope, as described above in connection with the other accessory components. The jaw 204 is operated by a handle 206 at its proximal end and can be used to provide a larger clamping force on targeted tissue than possible with the smaller devices that are able to be translated through a working channel of an endoscope. FIG. 10A shows the device being translated over the shaft 22 of the device of FIG. 1, by way of example only. FIG. 10B shows the jaws 204 being opened prior to reaching the distal tip 24, that has already engaged tissue. FIG. 10C shows the handle 206 has been closed and is locked via a ratchet arm 208. The handle 206 has a proximal hole 210 that allows the shaft 22 to be completely removed from the body while the oversheath embodiment 200 is left in place.

Other embodiments provide additional tools and imaging devices that could be passed over the anchoring catheter without the need to pass through an endoscope. These may include devices with snaring or cutting tools, additional optical systems, lighting or magnifying devices, feeding tubes, drains, flushing catheters or other therapeutic or medication or energy delivering devices that could be left in place after the anchor is detached and removed.

Figure 11B:
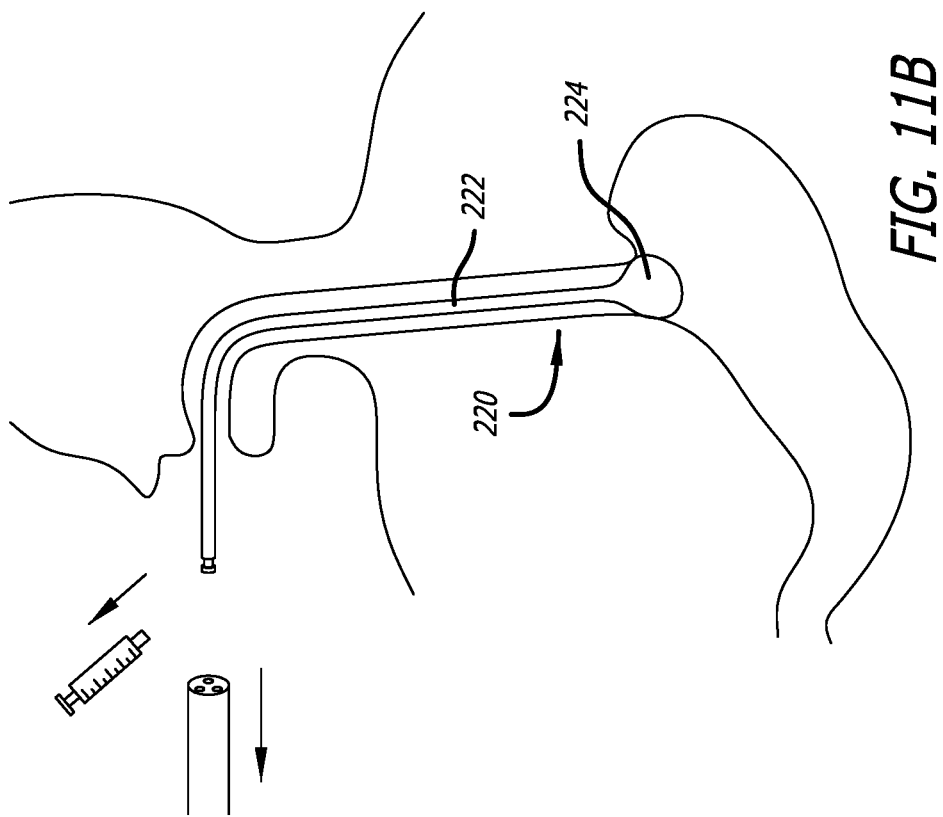
FIG. 11B is a perspective view of an embodiment of a device of the invention.
Figure 11A:
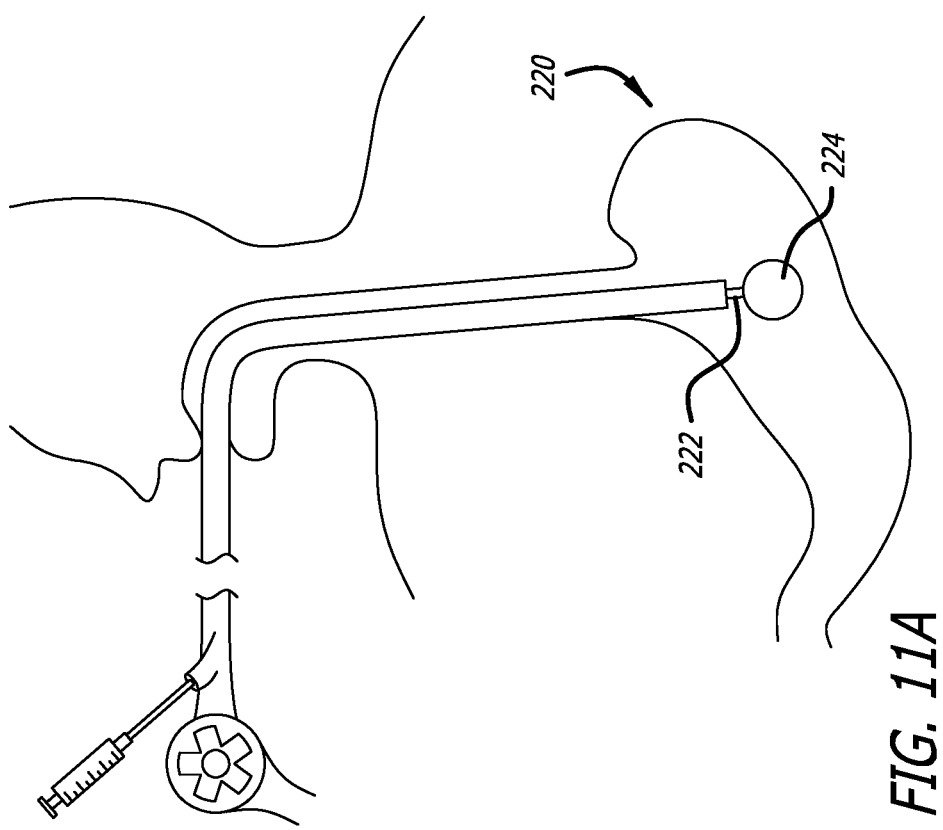
FIG. 11A is a perspective view of an embodiment of a device of the invention.

For example, FIGS. 11A-B show an inflatable balloon device 220 that can be delivered via an endoscope and left. The device has a shaft 222 with a lumen that is connectable to a syringe at a proximal and has a balloon 224 at its distal end. In FIG. 11A, the endoscope has been used to access the stomach and a syringe has been used to inflate the balloon 224. In FIG. 11B, the endoscope has been removed leaving the device 220 in place.

Figure 12B:
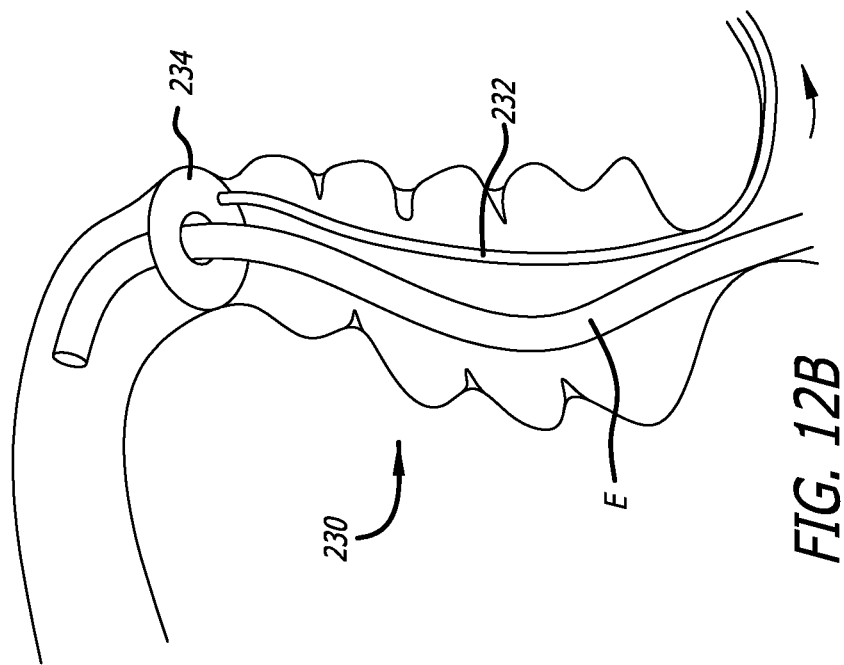
FIG. 12B is a perspective view of an embodiment of a device of the invention.
Figure 12A:
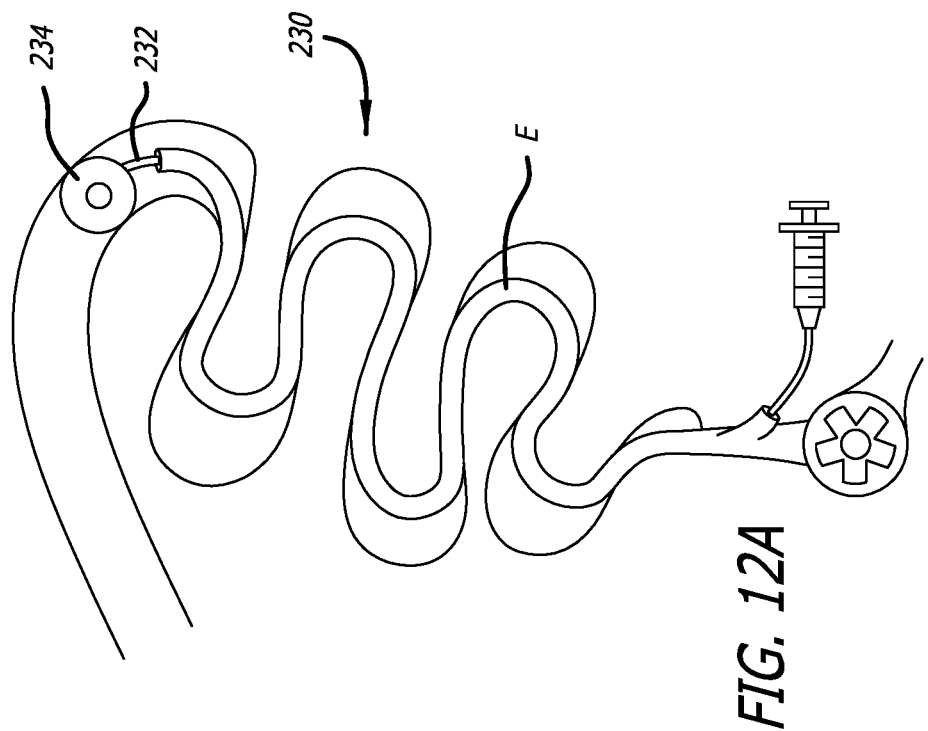
FIG. 12A is a perspective view of an embodiment of a device of the invention.

Balloons according to the invention could be used for a variety of purposes. For example, referring to FIG. 12, there is shown a balloon device 230 with a shaft 232 that terminates in a balloon 234 that has a donut or toroid shape. This embodiment differs from the embodiment 220 of FIGS. 11A-B only in the shape of the balloon. As seen in the Figures, the balloon 234 is advanced to a target site, such as an intestine, via an endoscope E and inflated (FIG. 12A). The endoscope E is then retracted over the device 230, which is left in place, and re-navigated to and through the balloon 234 as shown in FIG. 12B. The balloon thus is used to provide separation between the endoscope E and the walls of the intestine. This is beneficial for navigation and viewing purposes.

Figure 13:
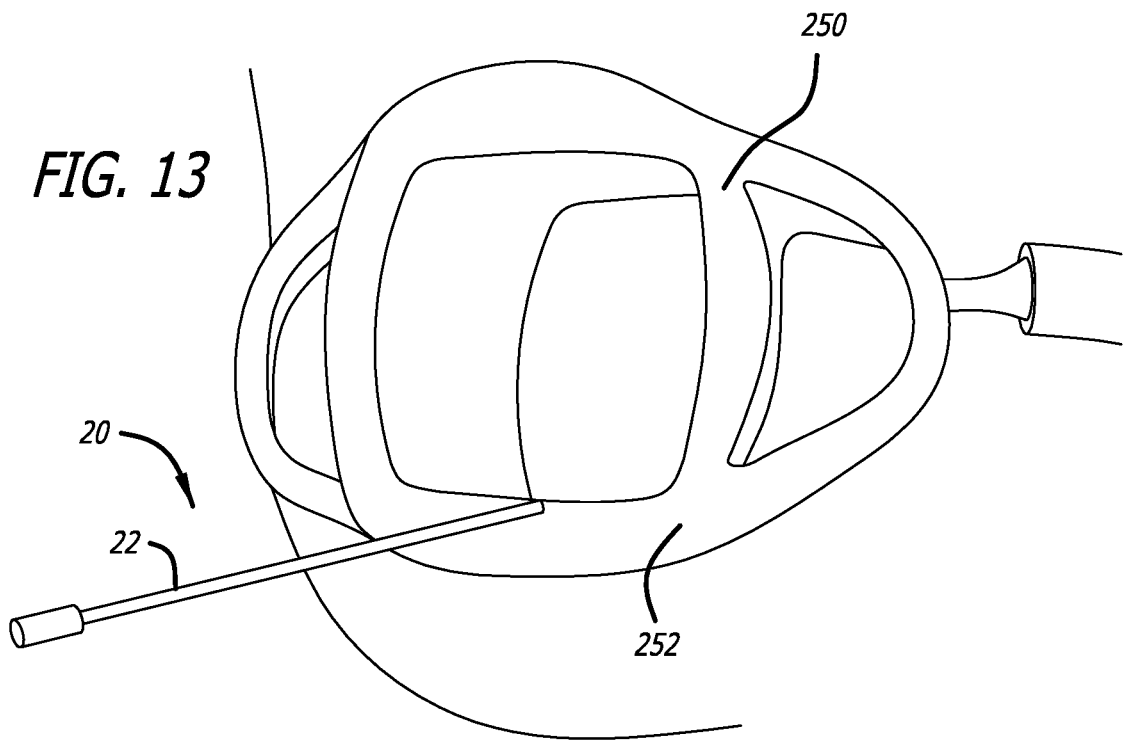
FIG. 13 is a perspective view of an embodiment of a device of the invention.
Figure 14:
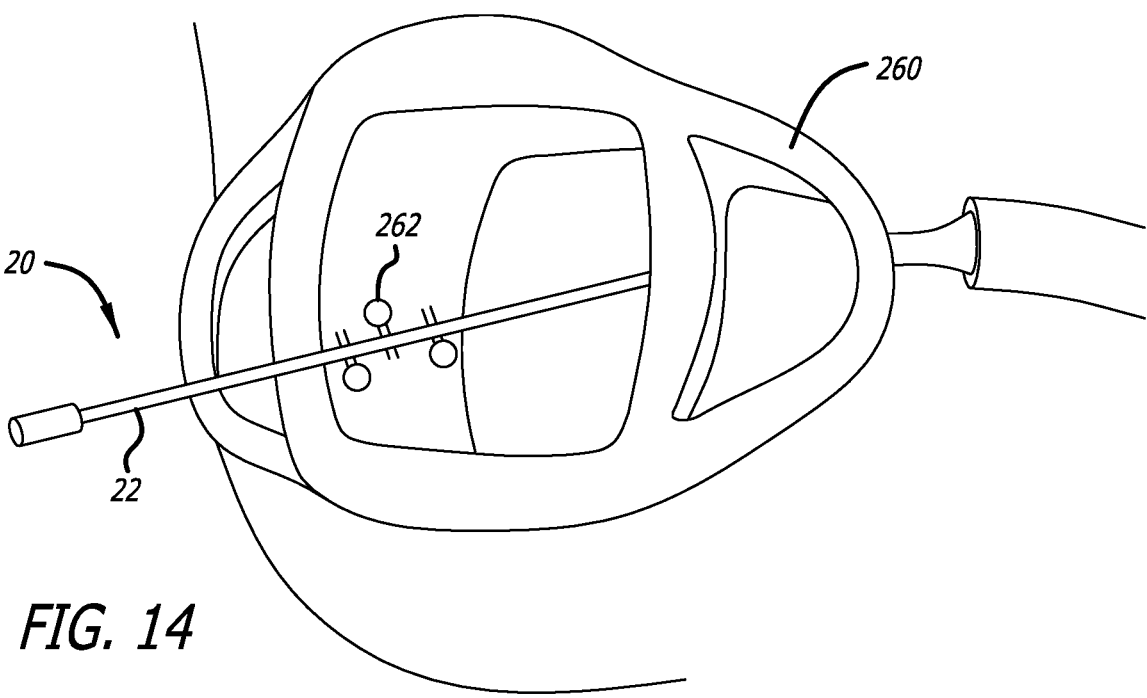
FIG. 14 is a perspective view of an embodiment of a device of the invention.
Figure 15:
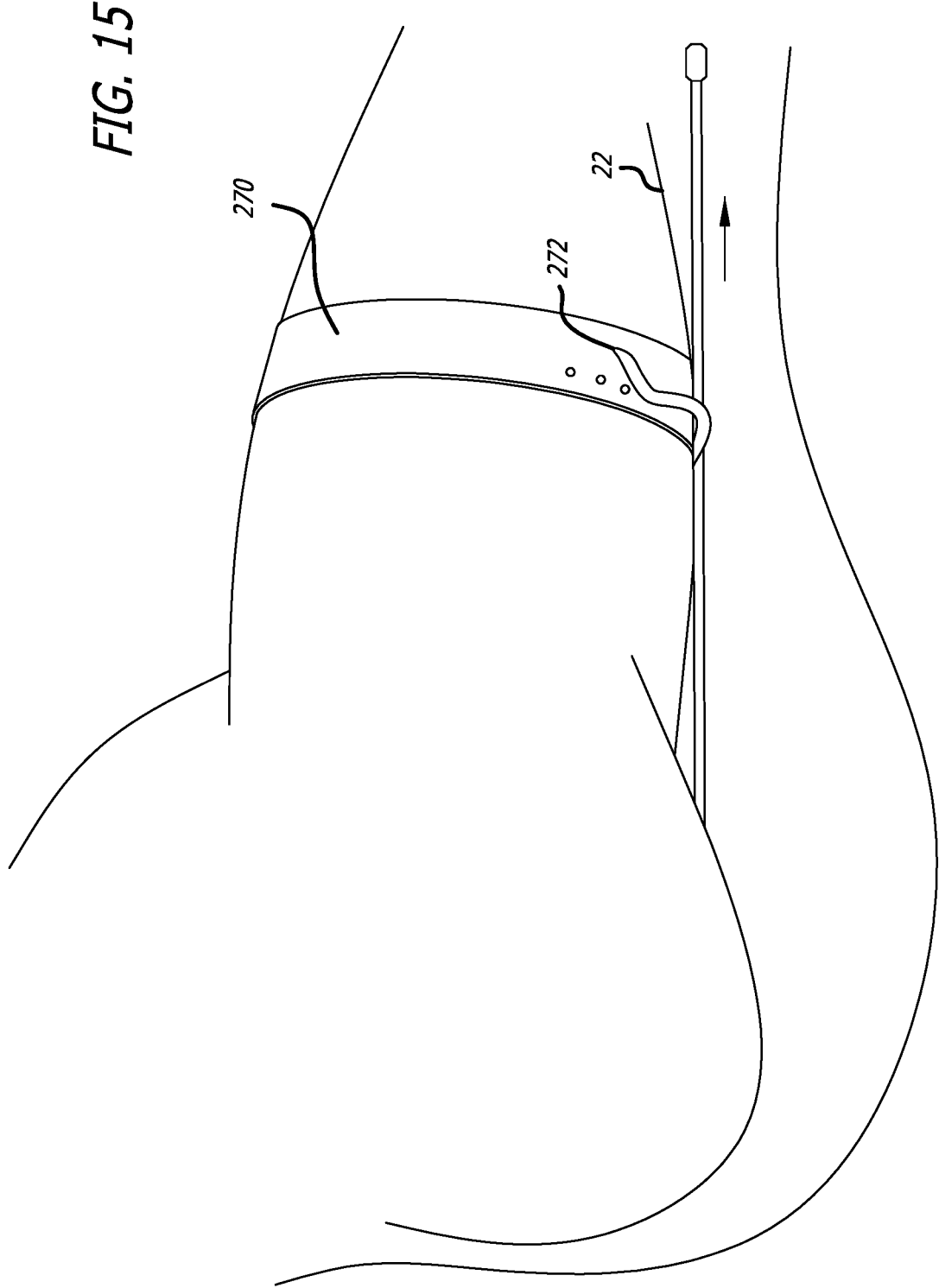
FIG. 15 is a perspective view of an embodiment of a device of the invention.
Figure 16:
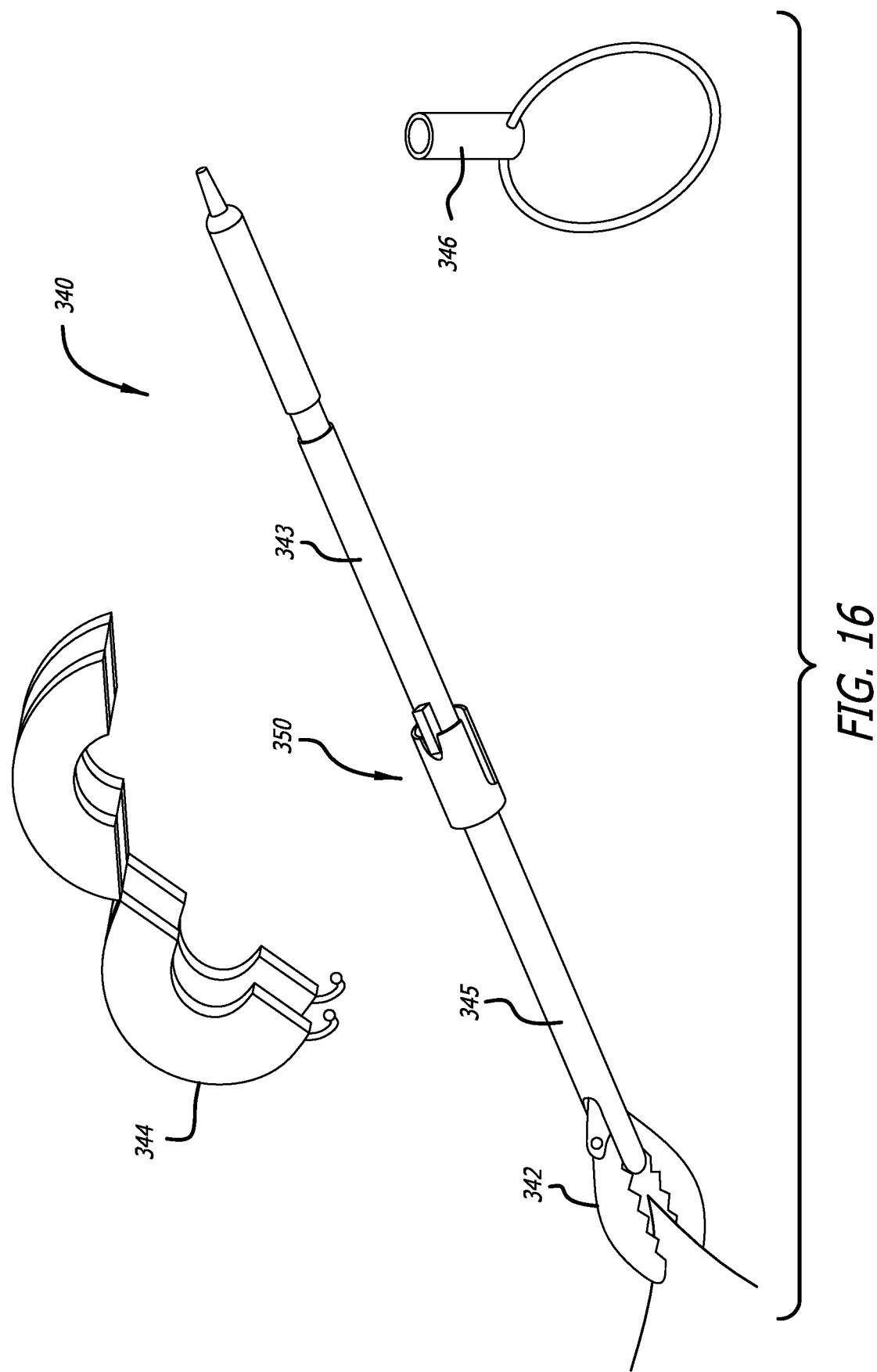
FIG. 16 is an exploded view of an embodiment of a device of the invention.

Other accessory components are shown in FIGS. 13-15 and pertain to ensuring the device does not get pulled or dislodged after in place and the endoscope is removed. FIG. 13 shows a mouthpiece 250 with a slot 252 formed in it. The mouthpiece is an elastomeric or flexible material such that the shaft 22 of a device 20 (using the device of FIG. 1 as an example) may be wedged into the slot 252 and held in place.

FIG. 14 shows an alternate embodiment 260 of a mouthpiece that has three hooks 262 formed there in for weaving the shaft 22 through to hold the device 20 in place.

FIG. 15 shows an embodiment 270 of a belt that may be used when holding a device 20 in place in a colo-rectal procedure. The belt fastens around the thigh of a patient and has a strap or other device 272 that is useable for holding the shaft 22.

Figure 21:
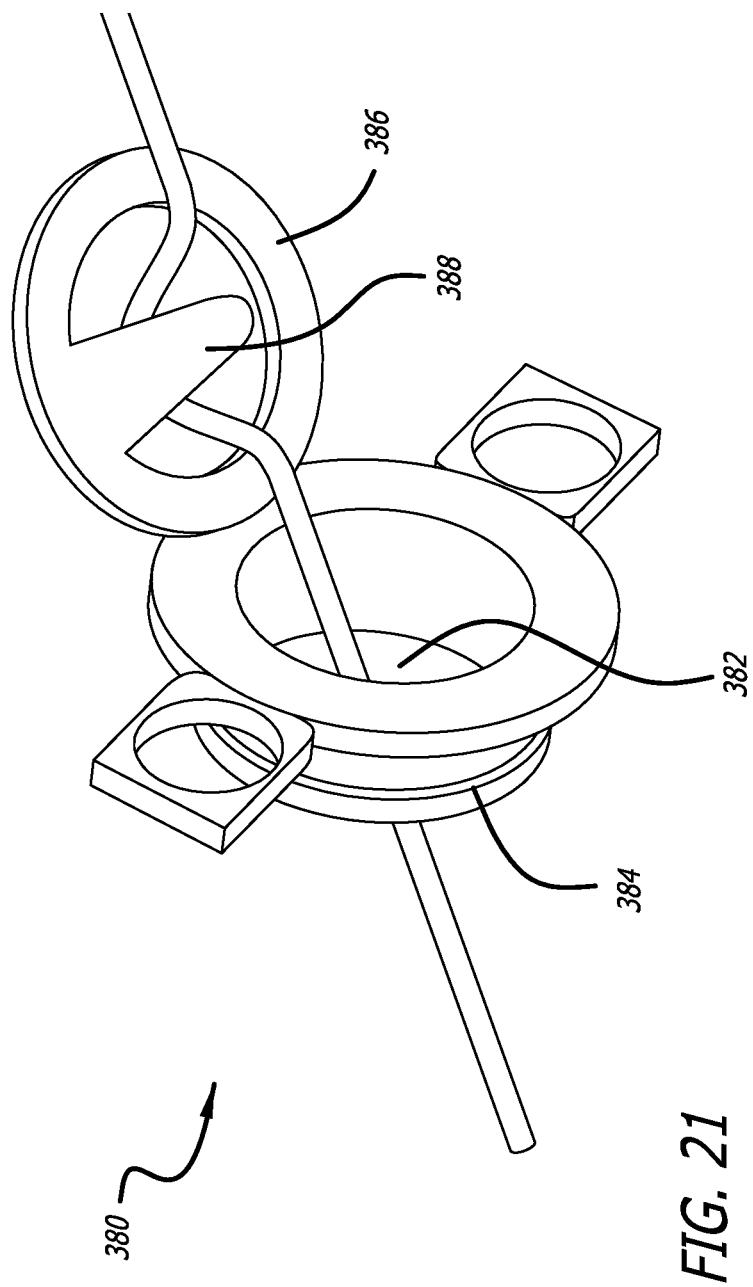

FIG. 21 shows an embodiment 380 of a mouthpiece that has a circular orifice 382 and a bite ring 384. The mouthpiece 380 is used with a circular stop 386 that is sized with a diameter larger than the circular orifice 382, such that the stop 386 cannot pass through the orifice and into the patient. A tab 388 protrudes into the center of the stop 386 and is used to attach to a device 390, as shown. The device 390 is simply a representation of any catheter-like medical device.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of manipulating tissue comprising:
   navigating an endoscope to a target location;
   advancing a device having a grasper at a distal end thereof through a working channel of the endoscope;
   using a handle at proximal end of the device to engage tissue with the grasper, the handle comprising an inner collet and an outer sleeve that tightens the collet around the device;
   locking the grasper using the handle such that the grasper remains engaged with the tissue, then;
   detaching the handle from the device while the grasper remains engaged with the tissue;
   retracting the endoscope over the device while leaving the device in place; and
   reattaching the handle to the device, then;
   unlocking the grasper using the handle such that the grasper disengages the tissue; and
   removing the device from the target location.

2. The method of claim 1 further comprising advancing the endoscope back to the target location alongside the device.

3. The method of claim 2 further comprising viewing the tissue using the endoscope while manipulating tissue with the device.

4. The method of claim 1 wherein using the device to manipulate tissue comprises advancing an oversheath over the device and using a feature at a distal end of the oversheath to manipulate tissue.

5. The method of claim 4 further wherein using the feature at the distal end of the oversheath to manipulate tissue comprises using a handle at a proximal end of the oversheath to control the feature at the distal end.

6. The method of claim 1, wherein the step of unlocking the grasper comprises engaging a protuberance within a slot of the device.

7. The method of claim 6, wherein the step of locking the grasper comprises disengaging the protuberance from the slot of the device.

8. A method of manipulating tissue comprising:
navigating an endoscope to a target location;
advancing a device having a grasper at a distal end thereof through a working channel of the endoscope;
engaging tissue at the target location by grasping the tissue with the grasper using a handle at proximal end of the device;
locking the grasper by engaging a twist-lock mechanism such that the grasper remains engaged with the tissue, then;
detaching the handle from the device while the grasper remains engaged with the tissue;
retracting the endoscope over the device while leaving the device in place;
reattaching the handle to the device, then:
unlocking the grasper by disengaging the twist-lock mechanism such that the grasper disengages the tissue; and
removing the device from the target location.

\* \* \* \* \*